(12) United States Patent
Moran

(10) Patent No.: US 7,077,372 B2
(45) Date of Patent: Jul. 18, 2006

(54) LOCKING ASSEMBLY FOR MOUNTING A DEVICE TO A SOLID SURFACE

(75) Inventor: Eric M. Moran, Camano Island, WA (US)

(73) Assignee: Control Dynamics, Inc., Everett, WA (US)

( * ) Notice: Subject to any disclaimer, the term of this patent is extended or adjusted under 35 U.S.C. 154(b) by 0 days.

(21) Appl. No.: 10/996,551

(22) Filed: Nov. 23, 2004

(65) Prior Publication Data

US 2005/0121576 A1 Jun. 9, 2005

(51) Int. Cl.
*A47B 96/00* (2006.01)

(52) U.S. Cl. .......................... 248/222.11; 248/224.51; 248/221.11; 248/222.13; 24/597; 24/573.11

(58) Field of Classification Search .......... 248/222.11, 248/220.21, 205.1, 200, 221.11, 222.51, 222.52, 248/222.13, 224.7, 225.11, 225.21; 24/573.11, 24/597
See application file for complete search history.

(56) References Cited

U.S. PATENT DOCUMENTS

| | | | |
|---|---|---|---|
| 4,093,293 A | | 6/1978 | Huggett |
| 4,660,793 A | | 4/1987 | Mark |
| 4,720,611 A | * | 1/1988 | Ishii ........................ 200/61.61 |
| 4,789,128 A | | 12/1988 | Yang |
| 5,054,170 A | * | 10/1991 | Otrusina ................... 24/580.11 |
| 5,188,325 A | | 2/1993 | Hilty et al. |
| 5,201,858 A | * | 4/1993 | Otrusina ................... 24/573.11 |
| 5,347,693 A | * | 9/1994 | Otrusina ................... 24/573.11 |
| 5,620,120 A | * | 4/1997 | Tien ............................ 224/199 |
| 5,622,296 A | * | 4/1997 | Pirhonen et al. ............ 224/197 |
| 5,850,996 A | | 12/1998 | Liang |

(Continued)

OTHER PUBLICATIONS

Allen-Bradley, Bulletin 700-HK "Slim Line" Relay, Cat. No. 700-HN122.

(Continued)

*Primary Examiner*—Robert P. Olszewski
*Assistant Examiner*—Todd M. Epps
(74) *Attorney, Agent, or Firm*—Kathleen T. Petrich

(57) ABSTRACT

A locking assembly having a substantially joined bracket assembly with a front and back plate defining an opening therebetween with a top slot and a side slot. At least the back plate is directly or indirectly fixedly attached to a solid surface. Positioned within side slot is a pivoting release lever having an upper leg and lower leg movable about a pivot. The pivot is fixedly attached to the front and back plates such that the upper and lower legs are free to move within the opening between the front and back plates within a defined boundary about the pivot. The locking assembly further includes a collar assembly having a collar assembly plate of a size and shape to fit edgewise and be guided into the opening between the front and bottom plates via the top slot. A collar extending from the front surface of the collar assembly plate is attached to a device. The upper leg of the pivoting release lever is positioned adjacent the inserted collar assembly plate and collar in order to pivot and restrain movement of the collar assembly (and device) when the collar assembly plate and collar are inserted into the opening and a front plate opening of the bracket assembly. When a force is applied to the pivoting release lever, the lower leg of the pivoting release lever acts to dislodge the plate and collar (and device) from the openings within the bracket assembly.

35 Claims, 14 Drawing Sheets

U.S. PATENT DOCUMENTS

| | | | |
|---|---|---|---|
| 6,059,156 A | 5/2000 | Lehtinen | |
| 6,098,858 A | 8/2000 | Laugesen | |
| 6,155,524 A | 12/2000 | Legler et al. | |
| 6,189,489 B1 * | 2/2001 | Pearce | 119/477 |
| 6,371,424 B1 * | 4/2002 | Shaw | 248/222.12 |
| 2005/0092801 A1 * | 5/2005 | Hicks et al. | 224/547 |
| 2005/0121576 A1 * | 6/2005 | Moran | 248/222.11 |

OTHER PUBLICATIONS

Lion Country Supply, Nelson Model 1400 Dog Feeding Pan, 2004, Web site: lcsupply.com.

* cited by examiner

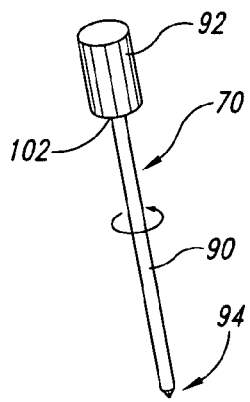
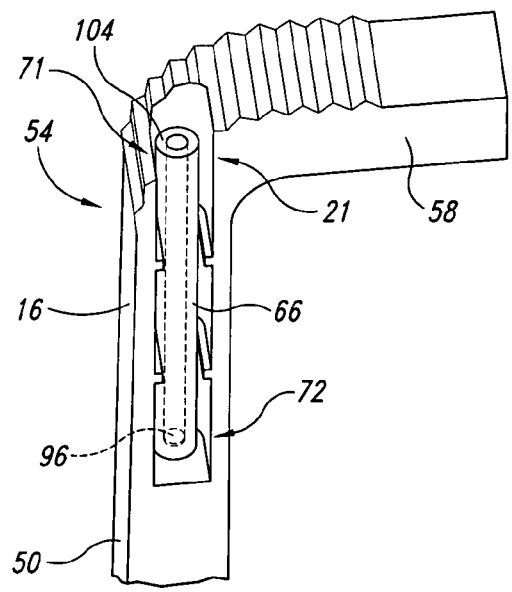
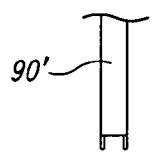
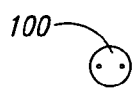
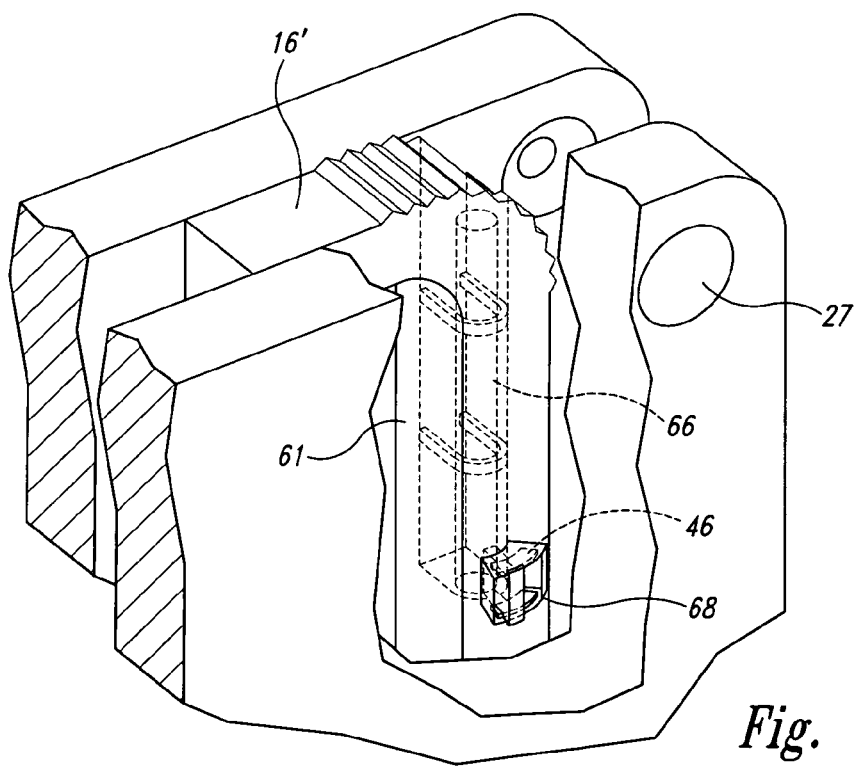
Fig. 13    Fig. 12    Fig. 15
Fig. 14    Fig. 16
Fig. 17

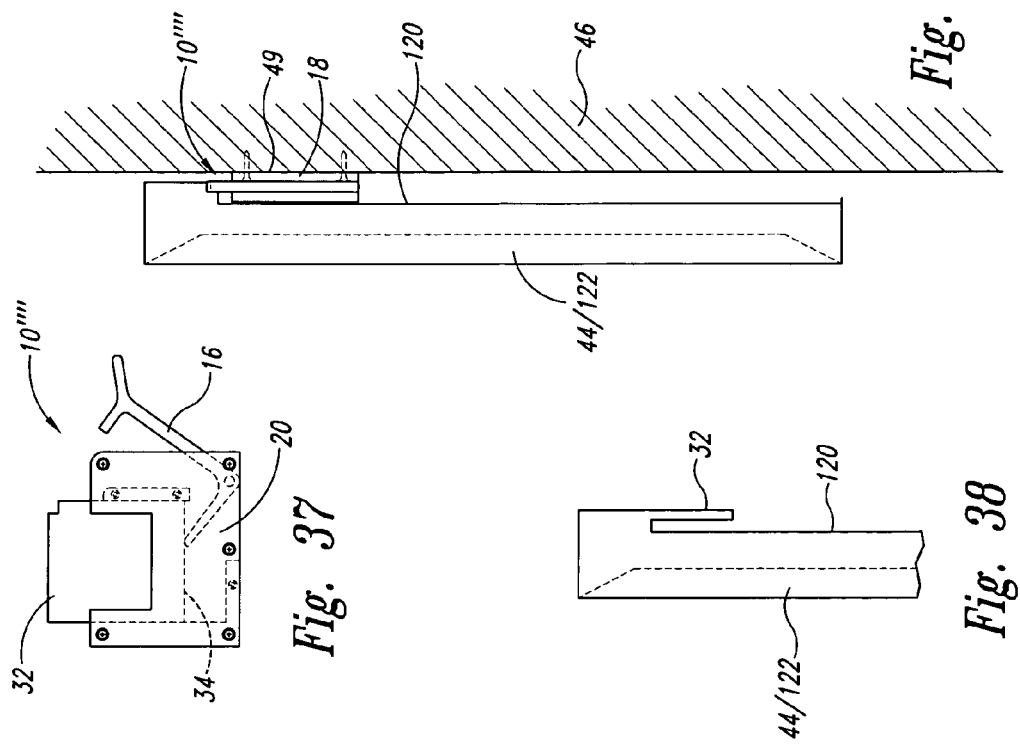
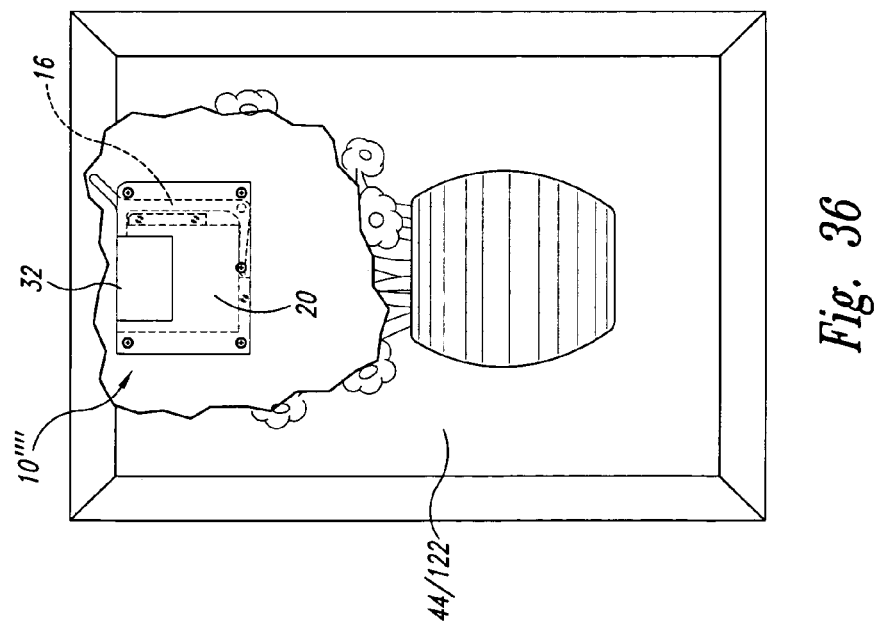

US 7,077,372 B2

LOCKING ASSEMBLY FOR MOUNTING A DEVICE TO A SOLID SURFACE

TECHNICAL FIELD

The present invention relates generally to locking mechanisms or assemblies. In particular, the present invention relates to a locking assembly with a pivoting release lever for mounting a device to a solid surface.

BACKGROUND OF THE INVENTION

Known locking mechanisms for mounting a device to a solid surface include convoluted mechanisms that have stored-energy springs or do not lock the device sufficiently to the solid surface. One such sliding latch is illustrated in the Nelson 1400 Dog Feeding Pan, in which a dog pan attached to a vertical surface (e.g., a wall). The sliding latch does not lock the device to the solid surface (wall) and can be knocked off by a rambunctious pet.

Moreover, known locking mechanisms do not have simplicity of design and ease of installation and dislodgment of a device, yet provide sufficient locking capabilities for joining a variety of devices to a solid surface.

Furthermore, known locking mechanisms make audible noise when locked or latched, which may be problematic for particular applications, such as those involving military or other tactical maneuvers.

SUMMARY OF THE INVENTION

The present invention is directed to a non-stored energy, single motion, locking assembly for attaching and locking a device to a solid surface that is easy to operate and has minimal moving parts that can break or fail.

The locking assembly of the present invention includes a bracket assembly having a front plate and a back plate joined about a substantial periphery of the two plates to form an opening between the two plates and a top slot and a side slot contiguous with the opening. Positioned within the opening at the side slot is a pivoting release lever having an upper leg and a lower leg joined together about a pivot. The pivot is attached to the front and back plates to allow the upper and lower legs of the pivoting release lever to rotate within a defined boundary of the opening between the front and back plates about the pivot.

The locking assembly further includes a collar assembly having a collar assembly plate that is of a size and shape to be received edgewise into the opening between the front and back plates via the top slot. Attached to a front surface of the collar assembly plate is a collar that is attached to a device. The collar is of a size and shape to be received into an opening of the front plate adjacent the top slot such that at least a substantial portion of the collar assembly plate and the collar may be received within the opening between the front and back plates and within the opening of the front plate when the device is to be secured to the bracket assembly, of which at least the back plate is secured to a solid surface.

The pivoting release lever is positioned within the side slot adjacent the collar assembly plate. To lock the device to a solid surface, the collar assembly plate is received into the top slot such that a lower edge of the plate applies a force onto the lower leg of the pivoting release lever. This force, in turn, forces the upper leg to swing upwardly about the pivot. A hold-down flange, which extends inwardly of the opening and is attached to the upper leg, restrains the upper edge of the collar assembly plate from upward movement once the collar assembly plate is inserted into the opening. In this manner, the device is secured and locked to the bracket assembly, which is secured to the solid surface such as a wall, a column, or even a belt or vest. Thus, the device is locked to the solid surface.

To unlock and dislodge the collar assembly plate (and, ergo, the device) from the bracket assembly (and solid surface), a force is applied to the upper leg via the hold-down flange. The single motion of the pivoting release lever moves the lower leg upward to apply a dislodging force to the lower edge of the collar assembly plate. Thus, the collar assembly and device are unlocked from the bracket assembly and may be readily removed from the bracket assembly (and, ergo, the solid surface).

The locking assembly of the present invention encompasses several embodiments. One is for a tamper resistant locking means. Another encompasses various shaped collars. Yet another embodiment encompasses an adapter plate that is attached to the back surface of the back plate when the bracket assembly is being secured to a non-planar surface. And yet another embodiment allows the elimination of the collar altogether if the device has a free hanging flange that can function as the plate (such as for mounting heavily framed artwork to a wall).

Another feature of the present invention is that the locking assembly is substantially noiseless in use. The pivoting action of the pivoting release lever makes minimal noise such that the present invention is particularly applicable for tactical (e.g., military) maneuvers in which attaching and detaching a device to a belt or vest with little to no noise is highly desired.

These and other advantages will become more apparent upon review of the Drawings, the Best Mode For Carrying Out the Invention, and the claims.

BRIEF DESCRIPTION OF THE DRAWINGS

Like reference numerals are used to designate like parts throughout the several views of the drawings, wherein:

FIG. 12 is an enlarged partial perspective view of the pivoting release lever of FIG. 11 (rotated 180 degrees) illustrating the cylinder barrel of the pivoting release lever shown in cutaway;

FIG. 13 is a perspective view of a key by which to activate the pivoting release lever by insertion of the key into the cylinder barrel of FIG. 12;

FIG. 14 is a bottom plan view of a the key of FIG. 13;

FIG. 15 is a partial front view of an alternate embodiment of the key;

FIG. 16 is a bottom plan view of the key of FIG. 15;

FIG. 17 is an enlarged partial perspective view of the locking mechanism of the base assembly shown in cutaway for use with the tamper resistant pivoting release lever of FIG. 11;

FIG. 34 is a side view of the locking assembly of FIG. 1 utilized in securing a collar to a solid surface (a wall is shown) for supporting and securing a vase and the like;

FIG. 36 is a front view of a framed art piece being secured to a solid vertical surface through a fifth embodiment of the invention shown in cutaway;

FIG. 37 is a front view of the locking assembly of FIG. 36 illustrated in the detached and unlocked position;

FIG. 38 is a side view of the frame attached to a plate assembly; and

FIG. 39 is a side view of the frame of FIG. 38 with the plate assembly inserted and locked into the locking assembly of FIG. 36, which is secured to a wall.

BEST MODE FOR CARRYING OUT THE INVENTION

Figure 1:
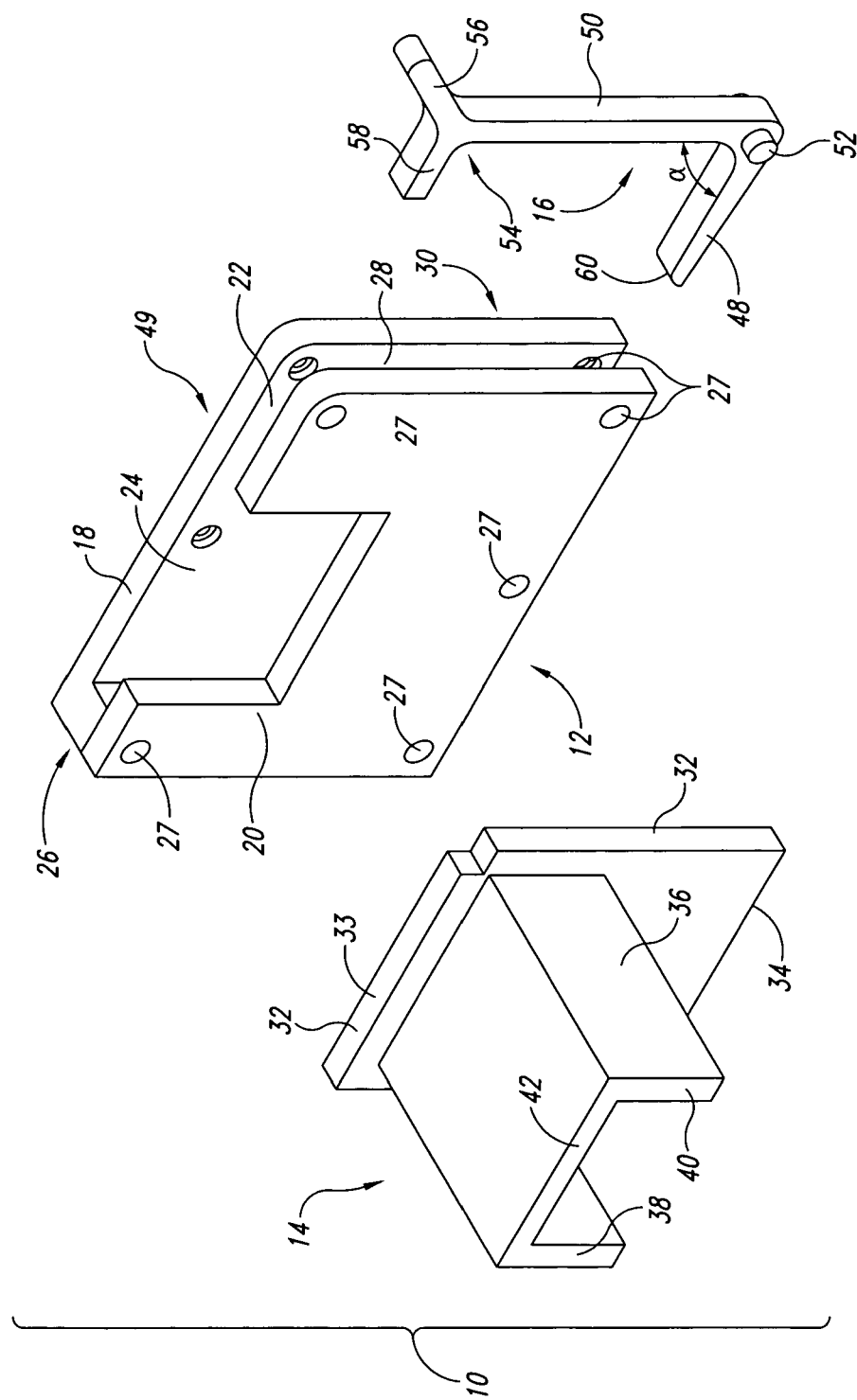
FIG. 1 is an exploded perspective view illustrating a bracket assembly, a pivoting release lever, and a collar assembly of the preferred embodiment shown less the fasteners.

The invention is directed to an improved locking assembly for mounting a device to a solid surface, such as a wall, floor, ceiling, column, table, belt or vest. The invention is not only easy to use and dislodge, but can do so making little noise.

Referring to FIGS. 1–8, the locking assembly 10 of the first embodiment includes a bracket assembly 12, and a corresponding collar assembly 14, and a pivoting release lever 16, that, when assembled, allows quick secure fixation and locking of the collar assembly to the bracket assembly through a single motion locking movement of the pivoting release lever. Similarly, dislodgement of the device and collar assembly can be equally easily obtained through the reverse action via the pivoting release lever.

The bracket assembly may be formed of a substantially rectangular back plate 18 and a substantially conforming mostly rectangular front plate 20 that are conjoined and spaced apart in such a way as to form a substantially continuous opening 22 between back plate 18 and front plate 20. Opening 22 forms a top slot 24 at the top 26 of bracket assembly 12 and a side slot 28 on one side 30 of the bracket assembly.

The front and back plates are joined together at portions of the peripheries of the two plates, with side slot 28 being accessible on one side, and the opposite side being joined to form an abutment edge 31, which will be discussed further below.

According to the preferred form, front plate 20 and back plate 18 are formed of two separate machined plates that are joined together primarily about portions of their peripheries by a plurality of fasteners 25, such as screws or rivets, which may be inserted into a plurality of openings 27. If screws are used to fasten the front and back plates together, openings 27 are preferably countersunk. Alternatively, the bracket assembly may be made of a unitary cast or molded piece in which the front and back plates are already joined substantially at the periphery of the two plates.

Collar assembly 14 includes a collar assembly plate 32 having an upper edge 33 and a bottom edge 34. Collar assembly plate 32 is of a size and shape to be received into top slot 24 such that bottom edge 34 of the collar assembly plate 32 substantially conforms to the shape of the top slot and that substantially all of the collar assembly plate 32 may be received edgewise within opening 22 via top slot 24. In preferred form, collar assembly plate is rectangular in shape with two planar and parallel surfaces and with the top and bottom edge surfaces also being rectangular in shape.

In addition to collar assembly plate 32, collar assembly 14 includes a collar 36 that is fixedly attached and extends outwardly from one side of collar assembly plate 32. Although the collar can be of many shapes, some of which are discussed in further detail below, the preferred shape of the collar is where the collar is fixedly attached substantially perpendicularly of the plate.

Figure 24:
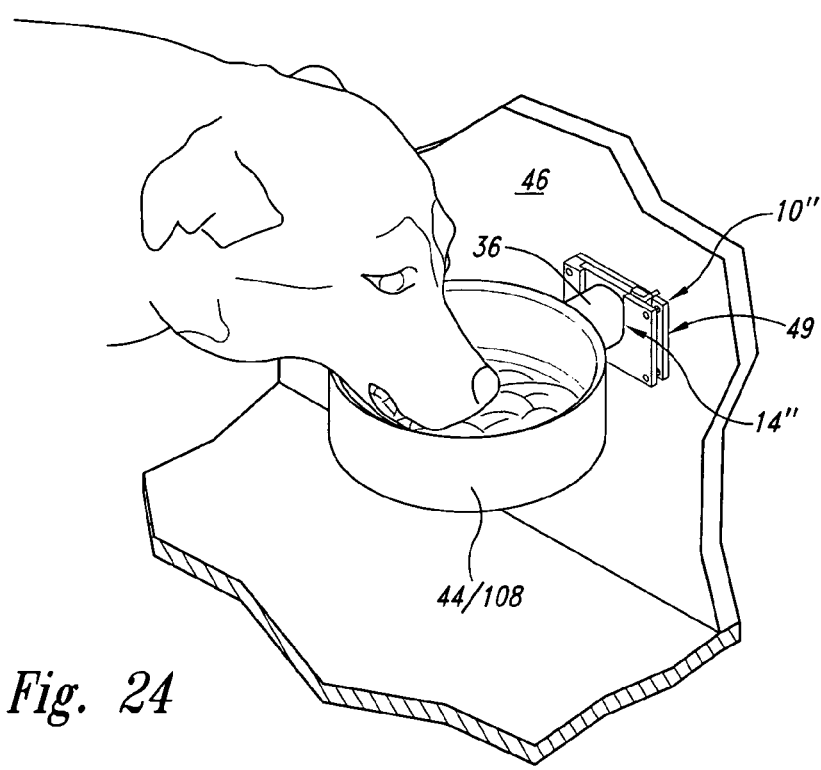
FIG. 24 is a perspective view of the locking assembly of FIG. 22 shown with a device (dog dish) fixedly attached to the collar assembly that is secured and locked to a solid surface (a wall)

In a first embodiment of the collar, the collar is comprised of a channel having two opposed sidewalls 38, 40 and a top wall 42 joined to and connecting upper surfaces of sidewalls 38 and 40. The collar 36 is attached to a device 44 (see FIG. 24 for example), of which can be varied and discussed further below, in order to readily secure and lock the device to a solid surface 46 (e.g., a wall as illustrated in FIG. 24), and, upon need, dislodge/unlock and remove the device from the solid surface.

Figure 2:
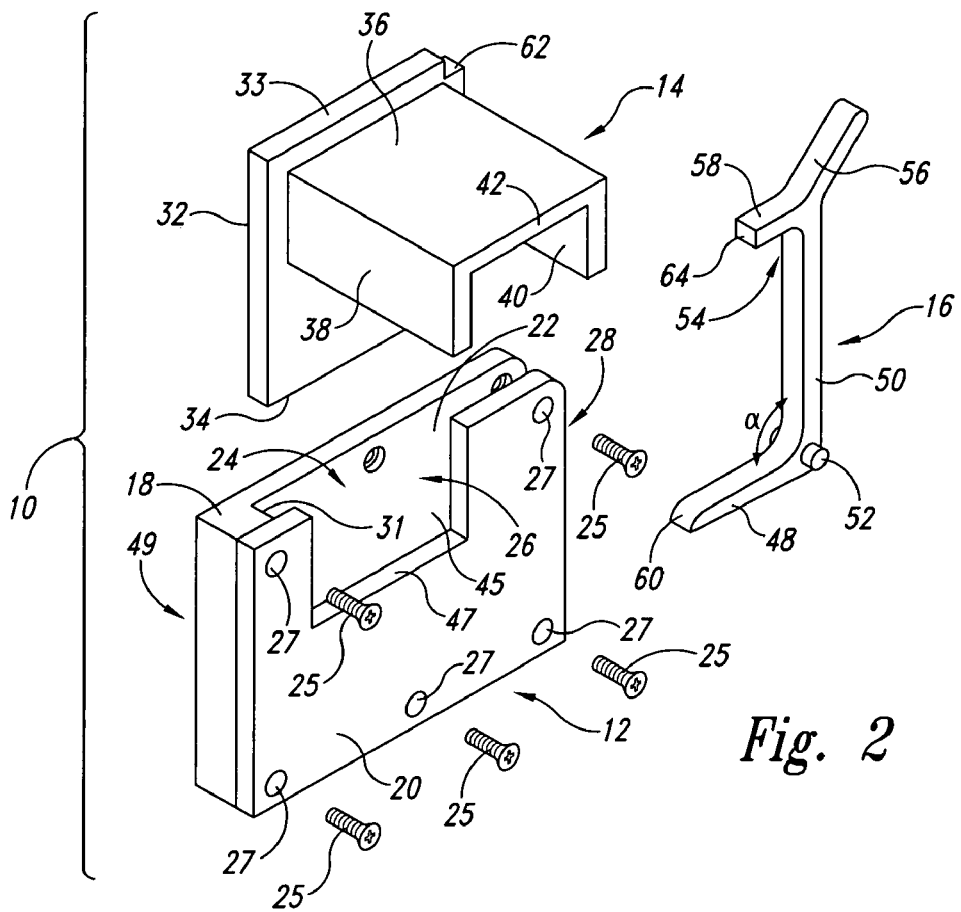
FIG. 2 is another exploded view of the substantially unassembled components of FIG. 1 except with fasteners.
Figure 3:
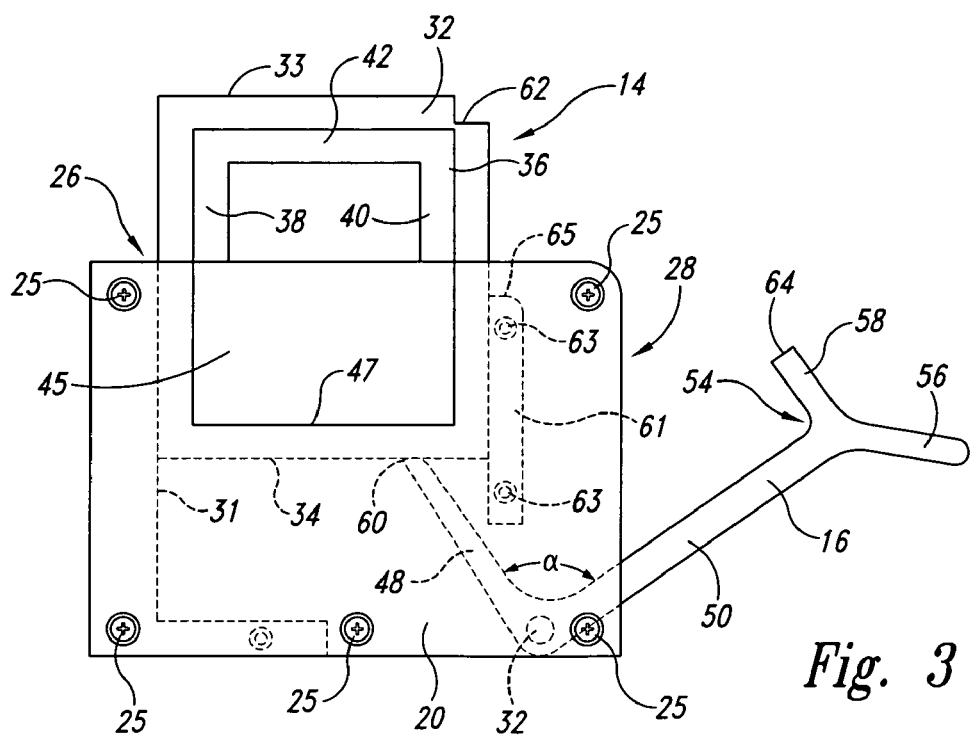
FIG. 3 is a front view of the assembled components of FIG. 2 in the nearly fully dislodged and unlocked position.
Figure 4:
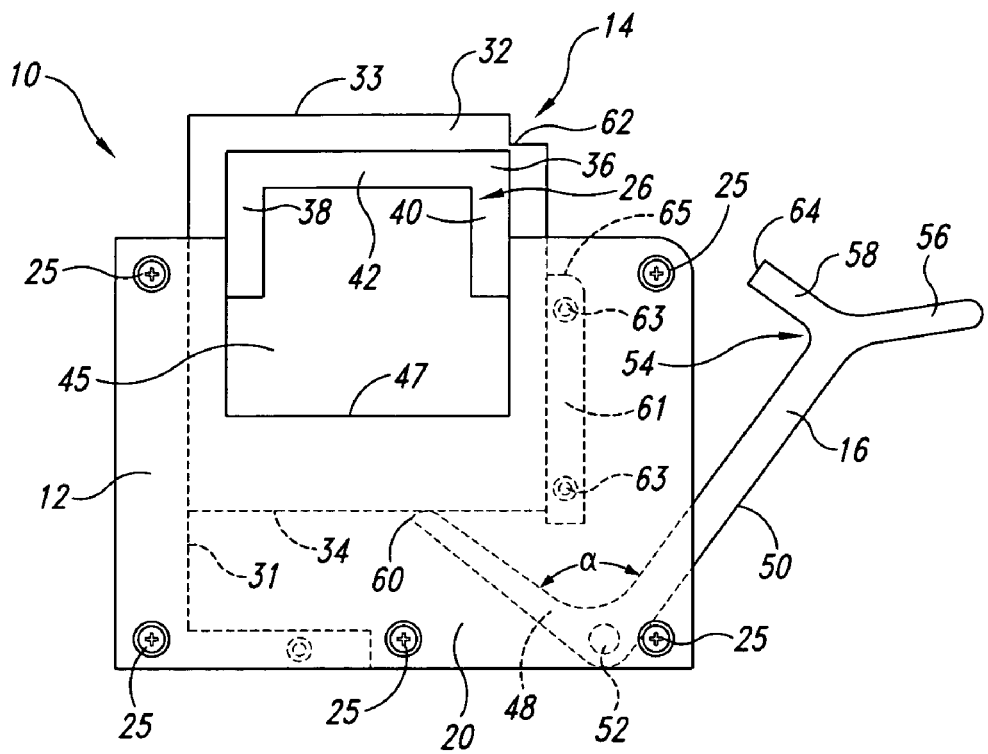
FIG. 4 is a front view similar to FIG. 3 where the assembled components are illustrated in the approximate half-way point of insertion or dislodge mode.
Figure 5:
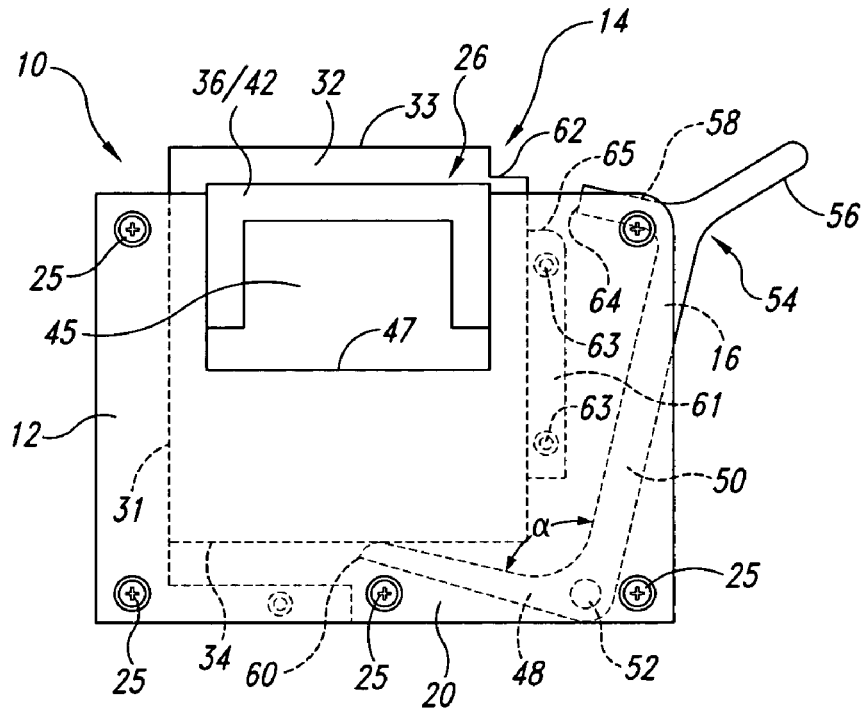
FIG. 5 is a front view similar to FIG. 3 where the assembled components are illustrated in the approximate ¾ of full insertion or approximate ¼ dislodge mode.
Figure 6:
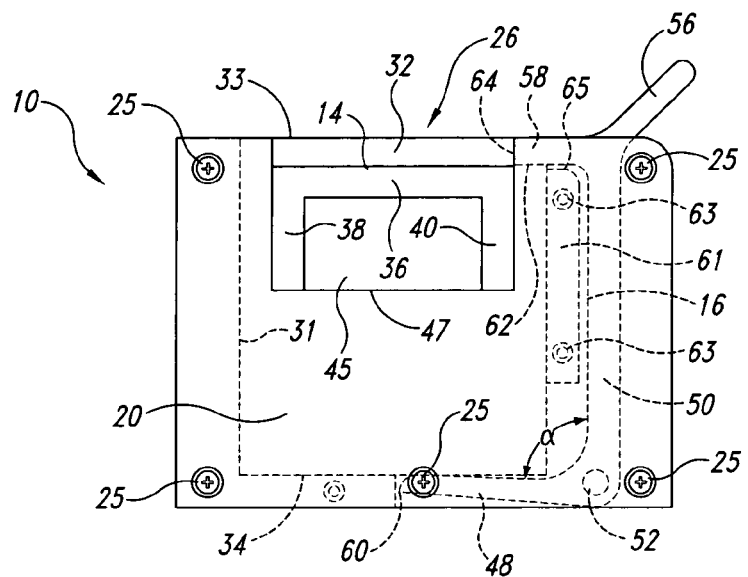
FIG. 6 is a front view similar to FIG. 3 where the assembled components are illustrated in the fully inserted and locked position.
Figure 7:
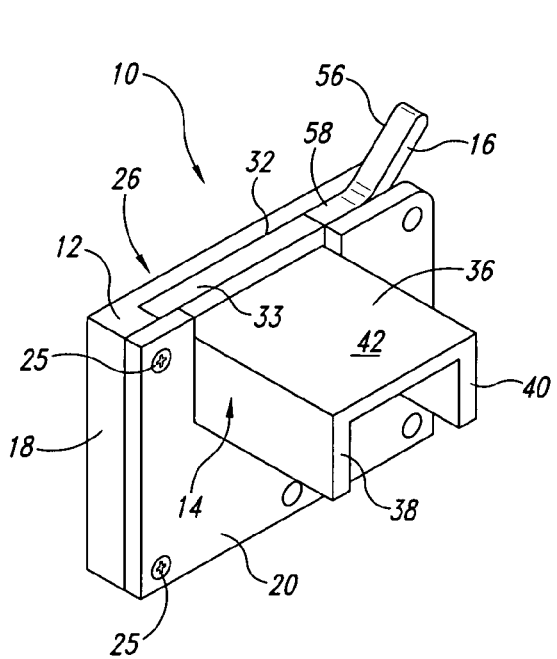
FIG. 7 is a perspective view of the assembled components of FIG. 1 in the fully inserted and locked position.
Figure 8:
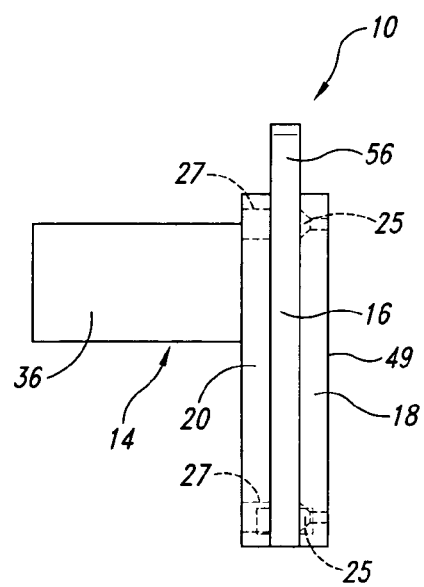
FIG. 8 is a right side view of the assembled components of FIG. 1 in the fully inserted and locked position.

As best illustrated in FIGS. 2, 3, and 6, the bottom edge 34 of collar assembly plate 32 is inserted into top slot 24 of bracket assembly 12, which is also preferably rectangular in shape. Collar 36 is of shape to be received with an opening 45 of front plate 20. Sidewalls 38, 40 abut a bottom edge 47 of opening 45 when collar assembly plate 32 is fully inserted into top slot 24.

The pivoting release lever 16 includes a first leg 48 and a second leg 50 to which a pivot 52 intersects the two legs. The two joined legs 48, 50 form substantially L-shaped angle α between the two legs at the pivot. In preferred form, the angle α is near or at 90 degrees to form an approximate "L" shape (or backwards "L") consisting of legs 48 and 50 and pivot 52. At the upper end 54 of leg 50 is a lip 56 and extending inwardly of the lever and leg 50 is an upper hold-down flange 58 that is used to secure (lock) the upper edge 33 of the collar assembly plate 32 within top slot 24.

Pivoting release lever 16 is positioned within opening 22 at side slot 26 between the back and front plates 18, 20 respectively. Pivot 52 is attached to the back and front plates, but still allowes rotational movement. Thus, pivot 52 secures pivoting release lever 16 to the back and front plates, but pivoting release lever 16 is free to move within opening 22 between the back and front plates 18, 20 about pivot 52 save for retaining structure discussed below.

Referring particularly to FIGS. 3–6, at the other end of pivoting release lever 16 is a distal end 60 of leg 48. Distal end makes contact with bottom edge 34 of collar assembly plate 32 during insertion and release (see FIGS. 4, 5, and 6). The insertion of the collar assembly plate 32 and collar 36 into the top slot 24 of opening 22 between the front and back plates of the bracket assembly, and retained by abutment edge 31 and an opposite situated elongated guide 61 applies a gravitational force onto the distal end 60 of leg 48. Guide 61 is preferably parallel to the abutment edge 31 and may be formed of a separated strip fastened between the front and back plates by fasteners 63 within opening 22 and near side slot 28. Guide 61 also functions as a restraining piece to aid in locking/latching the pivoting release lever in place as discussed further below.

When collar assembly plate 32 is inserted edgewise into top slot 24, bottom edge 32 of collar assembly plate 32 applies a force (in the preferred mounting form, a gravitational force) on leg 48 that necessarily moves leg 50 about pivot 52 resulting in leg 50 moving upward and inward within side slot 26. When the sidewalls 38, 40 of collar 36 makes contact with the bottom edge 47 of opening 45 of front plate 20, such as shown in FIG. 6, the bottom edge 34 of collar assembly plate 32 has applied maximum force to leg 48 of pivoting release lever 16. In doing so, leg 48 is positioned below bottom edge 34 and directly above the joined front and back plate periphery. Leg 50 is correspondingly positioned within side slot 26 and adjacent guide 61 with the hold-down flange 58 positioned over a portion of the upper edge 33 of collar assembly plate 32 and, preferably, guide 61. In this way, hold-down flange 58 locks/latches upper edge 33 of collar assembly plate 32 within the top slot 24 (FIG. 6). Thus, the collar assembly 14 secured and locked to bracket assembly 12. Because of the pivoting action of the release lever and the spatial relationship of the release lever relative to the plate and bracket assembly, the locking function is accomplished in a single motion.

The collar assembly is readily dislodged from the bracket assembly by the reverse procedure. When the collar assembly (and attached device) areis to be removed from the mounted bracket assembly, a force is applied to lip 56, which releases the hold-down flange 58 from restraining the upper edge 33 of collar assembly plate 32. At the same time, the force applied to lip 56 causes leg 48 to move upwardly of opening 22 such that the distal end 60 of leg 48 makes/forces the bottom edge 34 of collar assembly plate 32 to move upwards as the pivoting release lever 16 is moved in a downward motion. The release action is accomplished in single motion that simultaneously unlocks and dislodges the collar assembly for easy removal from the bracket assembly.

According to one aspect of the invention, a notch 62 may be formed of one side of the upper 33 of collar assembly plate 32 to accommodate the shape of the distal end 64 of the hold-down flange 58. As illustrated in FIGS. 1–6, notch may take the shape of a square to conform to a cube-shaped distal end 64. However, other corresponding shapes may be used and not deviate from the invention. This mating arrangement of the notch and distal end of the hold-down flange aids in keeping the upper edge 33 of collar assembly plate 32 restrained/locked until a force is applied to lip 56 to move pivoting release lever 16 and dislodge the collar assembly plate.

Guide 61 not only forms a barrier to which restrains collar assembly plate 32 from lateral movement toward side slot 62, but guide 61 may also function to restrain upper leg 50 of pivoting release lever 16 from rotational movement into the part of opening 22 that collar assembly plate 32 is received. The upper portion 65 of guide 61 is positioned adjacent and below hold-down flange 58 in order to support and guide the hold-down flange locking positioning over a portion of the upper edge collar assembly plate 32 (and preferably to mate with notch 62).

The pivoting release lever's single motion locking action, especially within the confines of the guide and shape of the hold-down flange of the upper leg relative to the positioning of the upper edge of the collar assembly plate, all perform (lock, dislodge) in relative quiet. This nearly noiseless feature has benefits discussed in more detail below.

As will be discussed further below, the back surface 49 of back plate 18 is fixed directly or indirectly to a solid surface 46, whether a wall, column, floor, ceiling, belt, or vest. For relatively planar solid surfaces, back surface 49 is preferably and directly secured to the planar solid surface by means of fasteners (e.g., screws, nails, rivets), or it may be adhered to the surface. Other well known fastening means for securing the back surface to the solid surface may be used as well. Securement of the bracket assembly to non-planar solid surfaces is discussed in more detail below.

The device is fixedly attached to the collar of collar assembly 14, whether through traditional fastening or adhesive means, or the device and collar are integrally formed. In either form, the device is fixedly attached to the collar assembly, which when locked into the bracket assembly securely locks the device to the solid surface until a user intends to dislodge the device from the solid surface.

Figure 9:
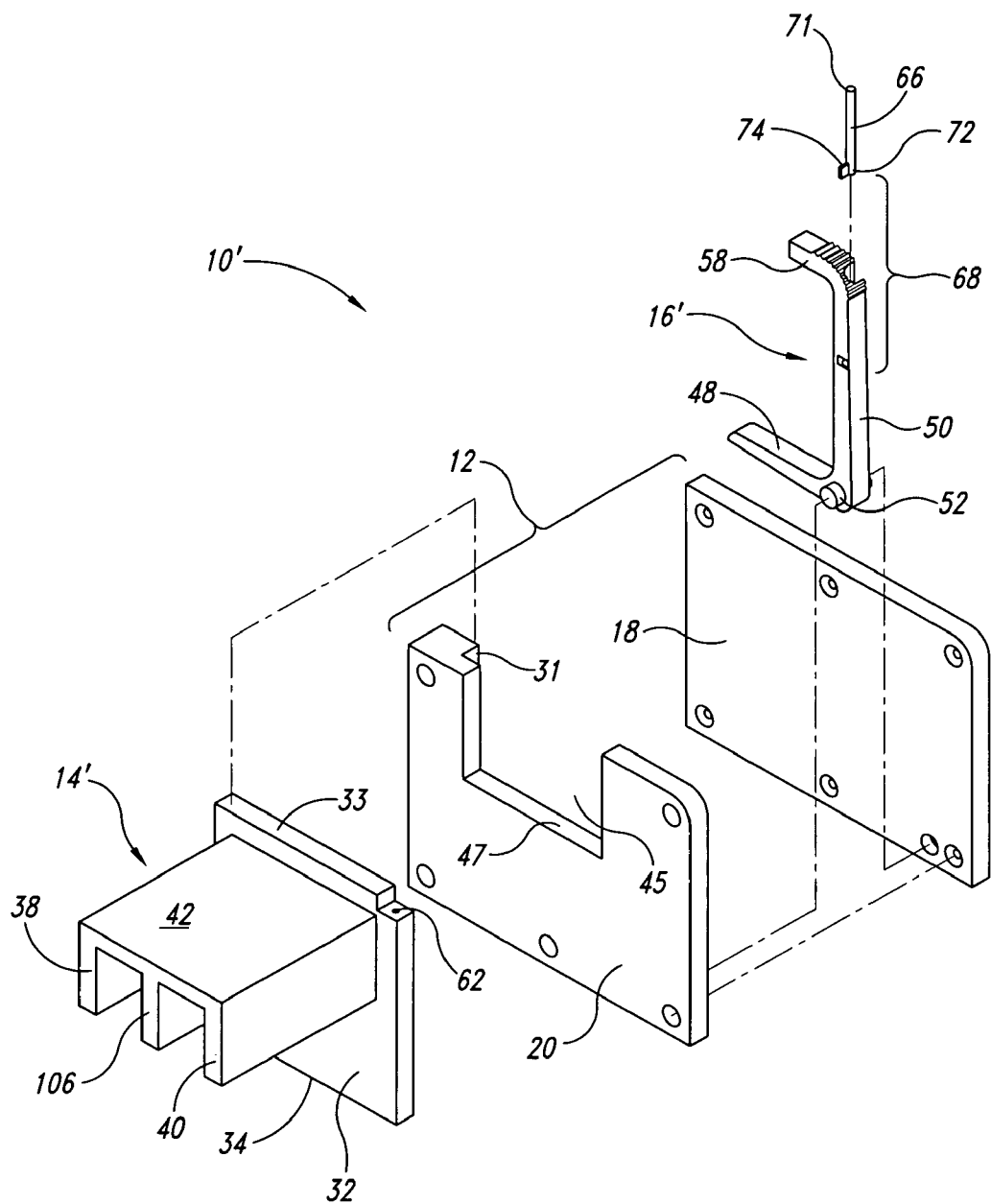
FIG. 9 is an exploded perspective view of a second embodiment having a tamper resistant pivoting release lever and a second embodiment collar assembly, shown less the fasteners.
Figure 10:
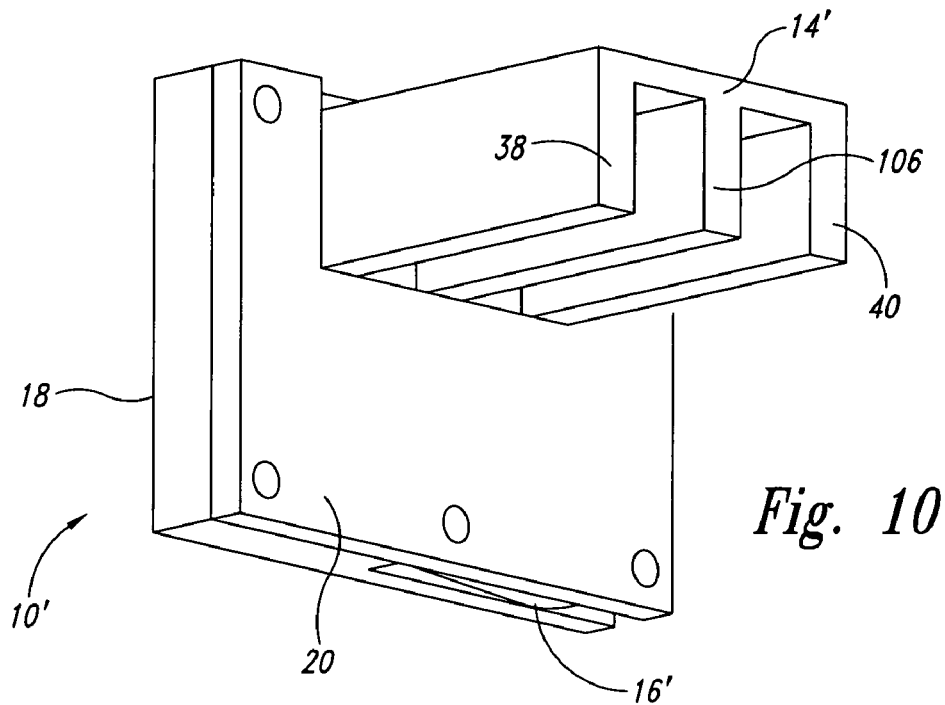
FIG. 10 is a perspective view of the embodiment shown in FIG. 9 except assembled.
Figure 11:
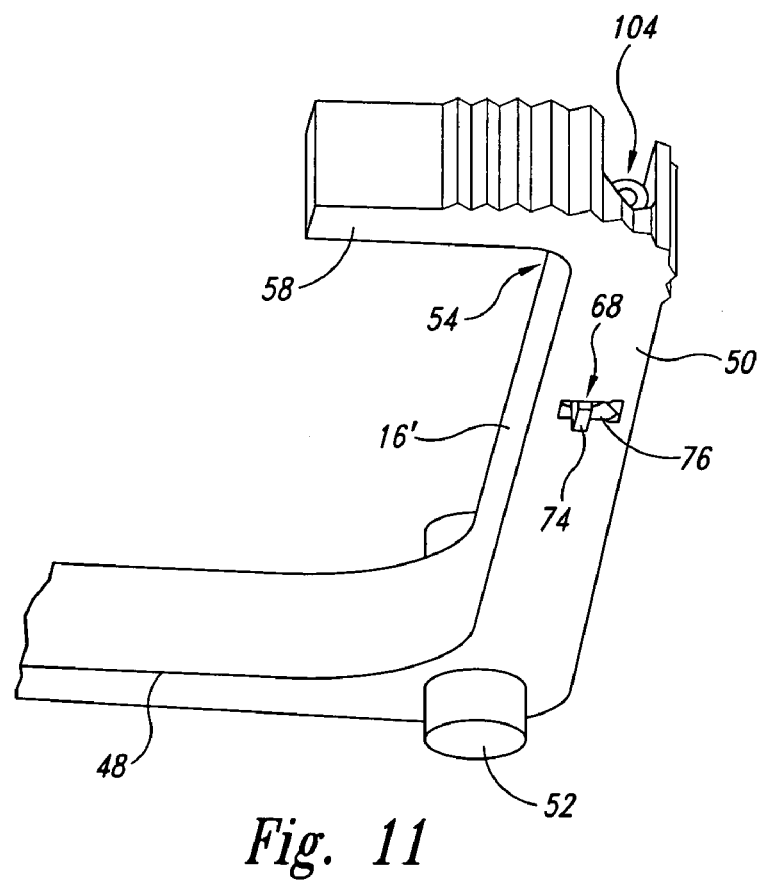
FIG. 11 is an enlarged top partial perspective view of the alternative tamper resistant pivoting release lever of FIG. 9.
Figure 20:
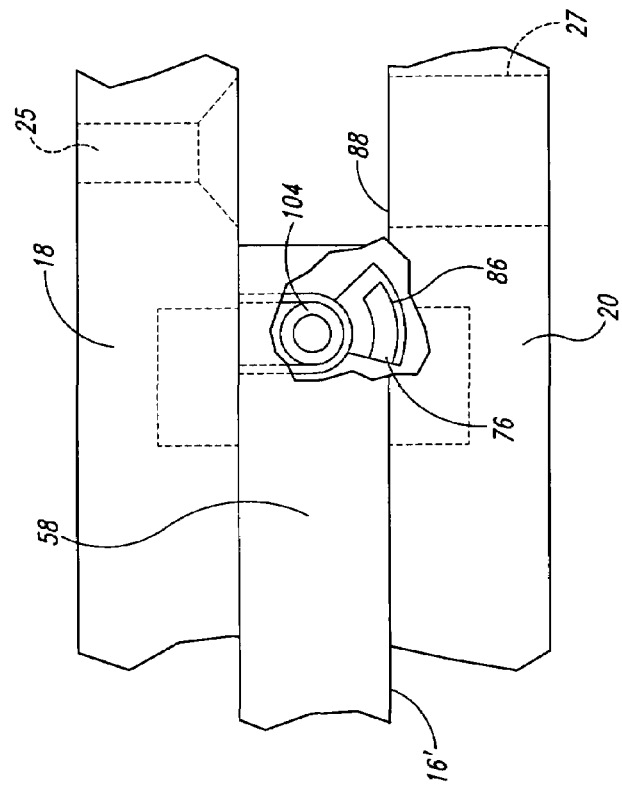
FIG. 20 is a partial top view of the assembled pivoting release lever locked to the front plate (locking mechanism shown in cutaway)
Figure 18:
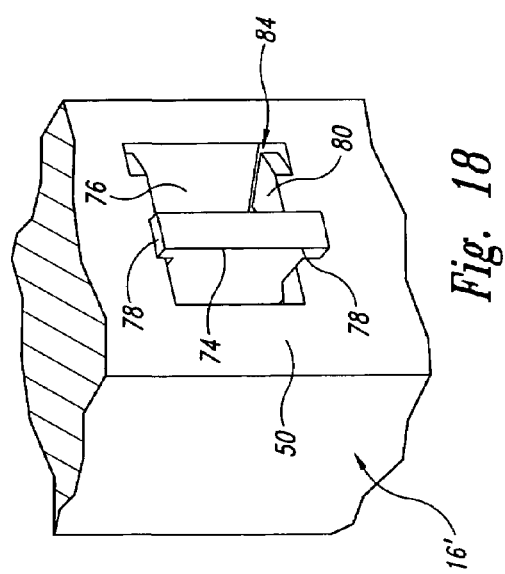
FIG. 18 is an enlarged perspective view illustrating the flange of the locking mechanism of the second embodiment in the locked position.
Figure 19:
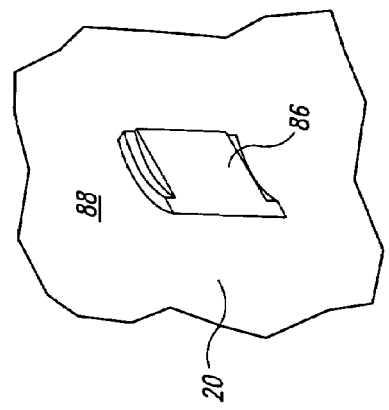
FIG. 19 is an enlarged partial perspective view of the back side of the front plate of the bracket assembly illustrating the catch to which the flange of FIG. 18 mates with to lock the pivoting release lever to the front plate of the bracket assembly.
Figure 22:
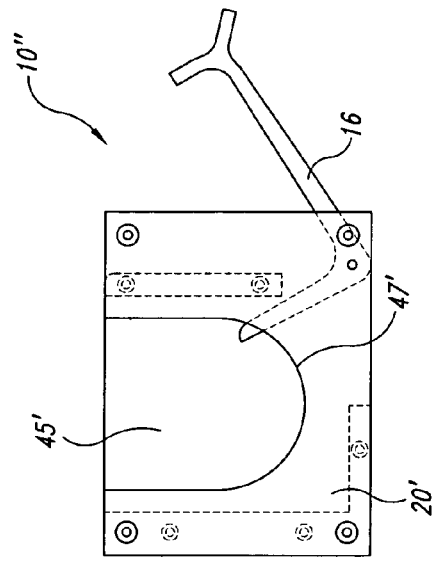
FIG. 22 is a front view of the assembled bracket assembly and pivoting release lever of FIG. 21.
Figure 23:
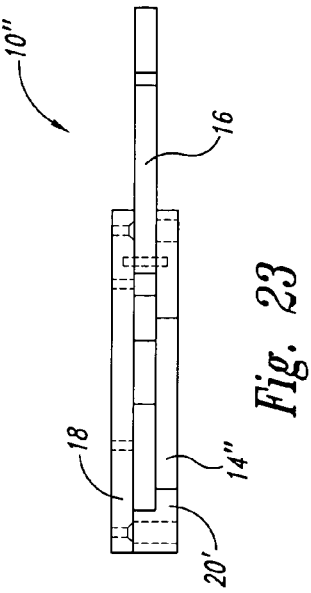
FIG. 23 is a top view of FIG. 22.
Figure 21:
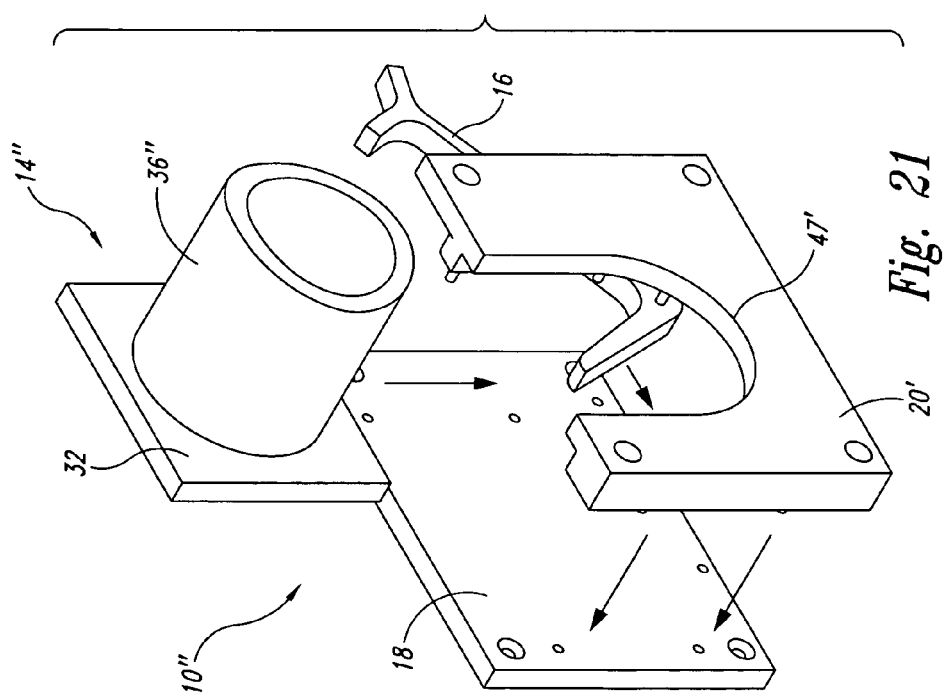
FIG. 21 is an exploded perspective view of a third embodiment of the bracket assembly and a cylindrical collar assembly, shown less the fasteners.

Referring now to FIGS. 9–20, a second embodiment of the invention 10' includes a tamper resistant pivoting release lever 16' in which the lip 56 of the first embodiment is eliminated and a tamper-resistant barrel 66 (FIGS. 9, 11, 12, and 17) and locking mechanism 68 are added (FIG. 9, FIG. 11, and FIG. 17).

Referring particularly to FIGS. 9, 11–13, and 17–20, barrel 66 which is illustrated in cylindrical shape, is of a shape to conform to a corresponding extending key 70 (FIG. 13). Barrel 66 includes top end 71 and bottom end 72. At the bottom end 72 is a flange 74 that is moved within a slot 76 between a locked and unlocked position. In preferred form, the flange 74 includes its own flange ends 78 and slot 76 includes a spacer 80 along most of the arc-like path that the flange 74 travels within the slot. At one end of slot 76, a rotational force must be applied to flange 74 in order to dislodge the flange 74 from space 84 to which the spacer 80 does not extend (where the flange 74 in unlocked relative to space 84 in slot 76 and allows rotational movement of the pivoting release lever 16' within opening 22).

Flange 74 with its own flanged ends 78 conforms to a catch 86 (FIG. 19) that is formed within a back surface 88 of front plate 20. When the flanged ends 78 of flange 74 are rotated in the locked position, they are restrained by catch 86 on the back surface of front plate 20, which restrains flange 74 (and ergo pivoting release lever 16') to front plate 20. Therefore, pivoting release lever 16' is locked into place with hold-down flange 58 positioned over the upper edge 33 of collar assembly plate 32, thereby locking the plate and the collar assembly to the bracket assembly.

Now referring also to FIGS. 14–16, key 70 consists of an elongated lower member 90 having a small cross-sectional area and an upper handle grip 92. Lower member 90 is of a shape to correspond and be inserted into barrel 66 and includes a distal end 94 having a specific shape that corresponds to small plate 96 at the base of barrel 66. Examples of such shapes are illustrated in FIGS. 14–16, such as a star notch shape 98 (FIG. 14) or a "snake eyes" shape 100 in FIG. 16 of an alternate distal end 90' shown in FIG. 15.

Upper handle grip 92 is of larger diameter (or surface area) than of the cross section of the lower member 90 in order to more readily access the handle grip and rotate the key during use and to position lower member 90 into barrel 66 a set length. At the base of upper handle grip 92 is a lower surface 102 that makes contact with the upper surface 104 of barrel 66 when the lower member 90 of key 70 is inserted into barrel 66.

The mating of the particular notched shape at the end of distal end 94 of key 70 with plate 96 of barrel 66 (within pivoting release lever 16') allows rotational movement in a step progression when a rotational force is applied to key 70 (e.g., turning the handle grip 92 is a clockwise direction to lock the flange 74 against catch 86 of front plate 20.

Although the collar assembly 14 illustrated in FIGS. 1–8 would work well in the tamper resistant embodiment of the invention, an alternate collar assembly 14' with an alternate collar 36' is shown in FIG. 9 in which a centrally positioned rib 106 is affixed or molded and positioned between sidewalls 38 and 40 in order to support a heavier object (discussed in further detail below) by dividing the load against three vertical members (supports) when the sidewalls and rib are applying a force onto bottom edge 47 of opening 45 within front plate 20.

In the locking mode, the collar assembly plate 32 of the collar assembly is inserted edgewise into top slot 24 between front and back plates 20, 18 similar to the locking operation of the first embodiment of FIGS. 1–8. The insertion and rotation of key 70 into barrel 66 with distal flange 74 rotationally moving between an unlocked and locked position within slot 76 and catch 86 of front plate 20 when the bottom of key 70 mates with barrel end plate 96. This action, in turn, restrains pivoting movement of the pivoting release lever 16' relative to the front plate.

To unlock the pivoting release lever and, thereby, dislodge collar assembly plate 32 (and ergo the collar assembly 14') from the bracket assembly, key 70 is inserted within barrel 66 and rotated the opposite direction from the movement made in the locking mode. Flange 74 is released from catch 86 and no longer restrained against front plate 20. Pivoting release lever 16' is free to pivot about pivot 52. If key 70 is still inserted into barrel 66, a user may use the handle grip of the key to position the pivoting release lever 16' about pivot 52 to apply a force on bottom edge 34 of collar assembly plate 32 to dislodge collar assembly 14' (or 14).

The hold-down flange may include a knurled outer radius, as best illustrated in FIGS. 9, 11, and 12, in which to better grip the hold-down flange in the absence of the lip of the first embodiment.

Referring now to FIGS. 21–24, a third embodiment of the invention 10" incorporates another collar assembly embodiment 14" in which the collar 36" is a cylindrical member attached to collar assembly plate 32. Corresponding to cylindrical collar 36" is opening 45' in front plate 20' in which the bottom edge 47' is rounded to restrain collar 36" securely into rounded bottom edge 47' when collar assembly plate 32 is inserted into opening 22 of the bracket assembly.

Referring now to FIG. 24, a main feature of the invention is the ease to which a device 44 may be readily attached and detached from a solid surface 46, such as a wall. FIG. 24 illustrates one of many devices 44 to which easy attachment and detachment to a wall or other solid surface is desirable. In that figure, a dog dish (device) 108 is fixedly attached to collar assembly 14". The entire dog dish can be readily attached to wall 46 by inserting the plate of the collar assembly into the top slot of the bracket assembly and locking the top edge of the plate by the hold-down flange of the pivoting release lever (in any of the embodiments discussed above). The locking assembly secures the dog dish to the solid surface (wall) more securely than known sliding latches. This locking assembly application is particularly useful for rambunctious pets or pets that are wearing conical collars as part of medical convalescence. Similarly, the dish is readily detached from the wall (for cleaning, refilling, etc.) by unlocking the pivoting release lever and applying a downward force on the lever to dislodge the plate and collar assembly from mounted bracket assembly.

At least the back plate of the bracket assembly is fixedly attached to a solid surface (e.g., wall, ceiling, floor) through a plurality of fasteners, such as elongated screws or rivets that go through openings 27 that also join front and back plates together, or through adhesives or epoxies, magnets, or through other conventional fastening techniques. The locking assembly of the present invention may be of various sizes, depending on the weight and size of the load being secured to the solid surface. For a small locking assembly carrying a relatively small weight, a single fastener may be utilized to secure at least the back plate to the solid surface.

Figure 25:
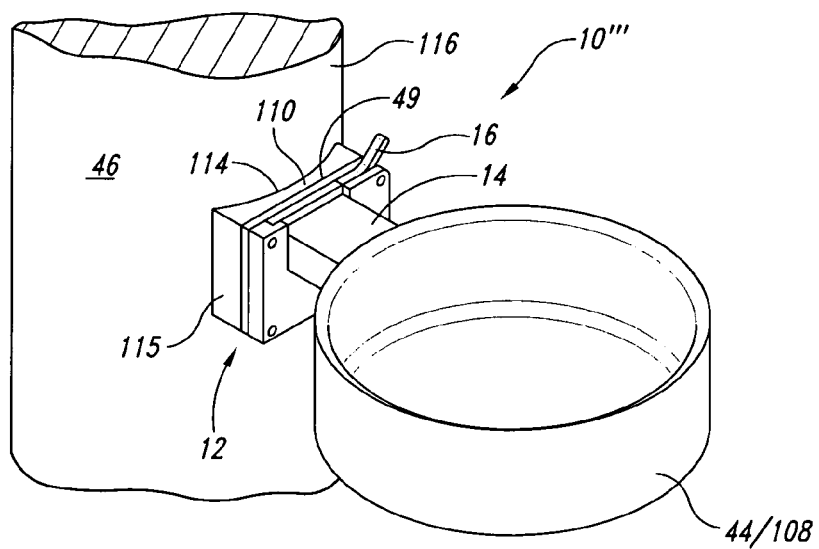
FIG. 25 is a perspective view of a fourth embodiment of the locking assembly illustrated with an adapter plate to conform to an non-planar surface.
Figure 28:
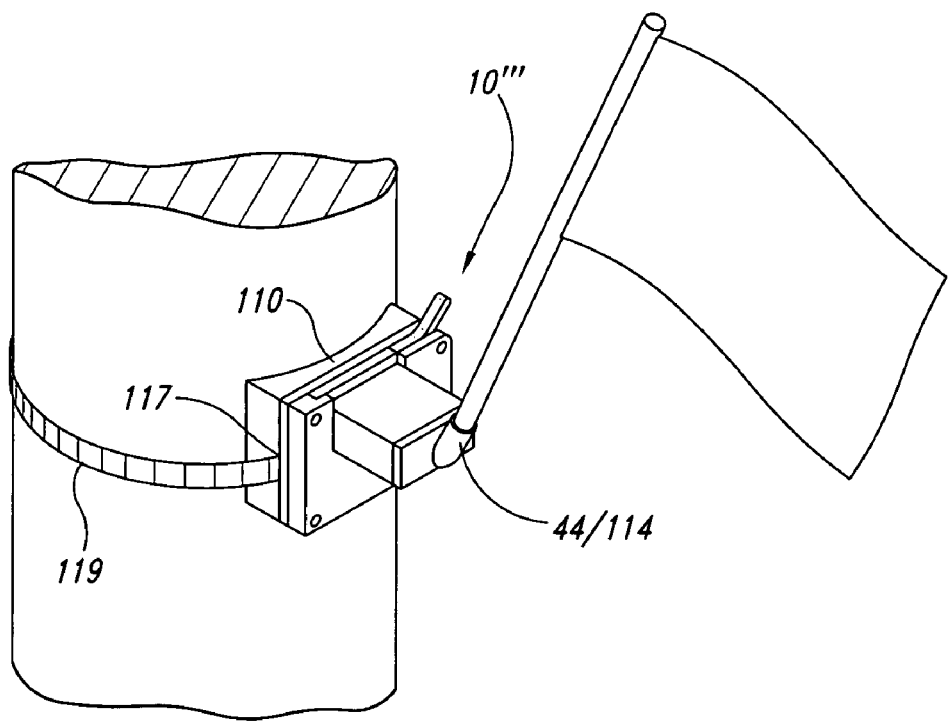
FIG. 28 is a perspective view of similar to FIG. 25 in which a device (a flag pole holder) is integrally formed with the collar assembly, and the bracket assembly is banded to a column via an adapter plate that includes a slot in which a band is thread side-to-side through the adapter plate.

Now referring to FIGS. 25–28, another embodiment of the locking assembly 10''' may include a non-planar adapter plate 110 to having a planar front side 112 and a non-planar back side 114 of a size to conform to a non-planar solid surface 116. The adapter plate is fixedly attached to the back surface 49 of back plate 18 of bracket assembly 12 (fastened or adhered in FIG. 25, through banding in FIG. 28). In the embodiment illustrated in FIG. 28, the adapter plate 110 includes a slot 117 of a size and shape to support a band or belt that enters one side of the adapter plate and exits out the other side. The non-planar back side 114 is then fastened, banded, or otherwise fixedly adhered to the non-planar surface (such as a column as illustrated in FIGS. 25 and 28) to which the device is desired to be attached. The non-planar back side 114 may be attached to the non-planar surface 116 as discussed above.

Figure 26:
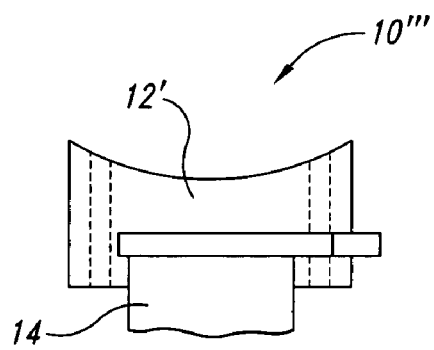
FIG. 26 is a top plan view of the locking assembly of FIG. 25 except that the base assembly and adapter plate are illustrated as an integral unit.
Figure 27:
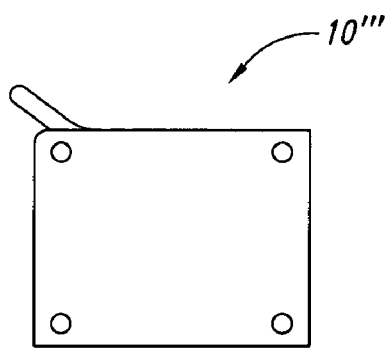
FIG. 27 is a rear view of the FIG. 26.

Although the non-planar adapter plate 110 provides maximum manufacturing flexibility, a unitary non-planar bracket assembly 12" may be molded or cast as illustrated in FIG. 26.

Figure 29:
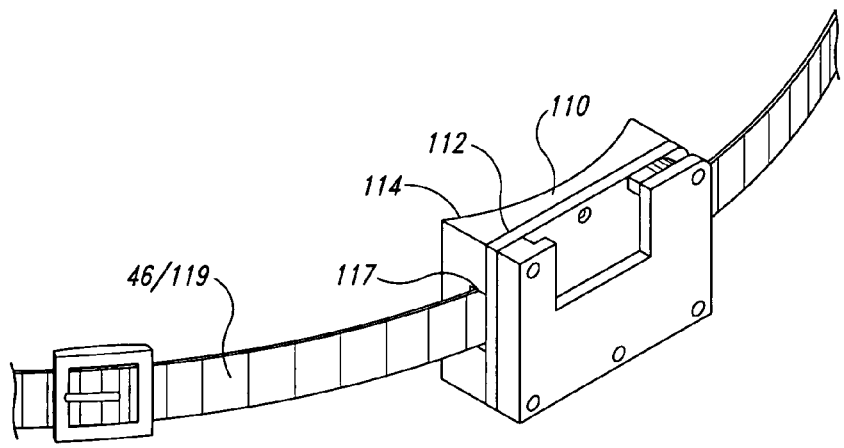
FIG. 29 is an enlarged view of the embodiment illustrated in FIG. 28, except that the band is a belt that can be worn by a person.
Figure 30:
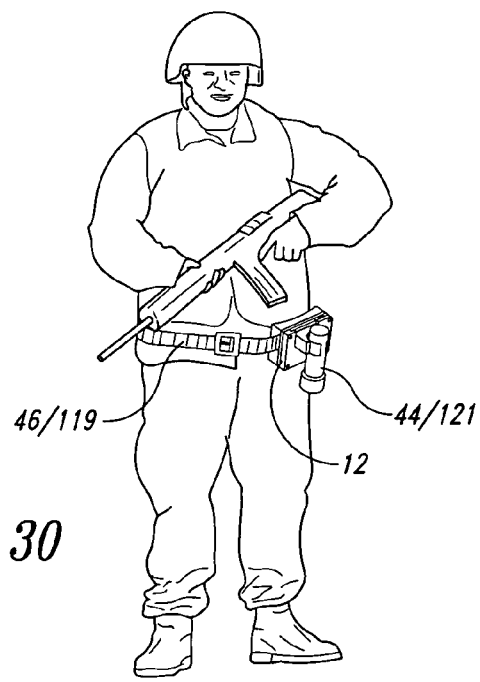
FIG. 30 is a perspective view illustrating a person wearing the belt and bracket assembly (shown exaggeratedly enlarged for clarity) of FIG. 29 with a flashlight integrally attached to the collar assembly.
Figure 31:
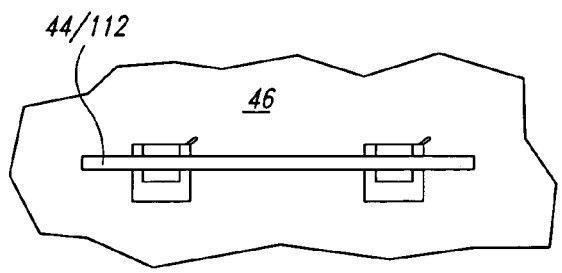
FIG. 31 is a front view of a shelf being supported and secured to an adjacent wall by a pair of spaced-apart locking assemblies as illustrated in FIG. 1.
Figure 32:
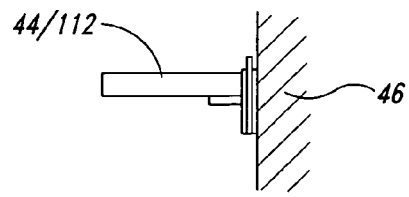
FIG. 32 is a side view of a FIG. 31.
Figure 33:
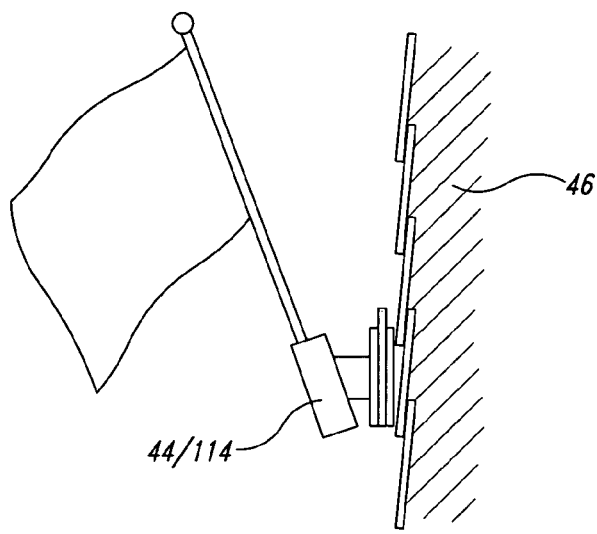
FIG. 33 is a side view of the locking assembly of FIG. 1 utilized in securing a rod holder (flag pole holder) to a solid surface (exterior wall of a house)
Figure 34:
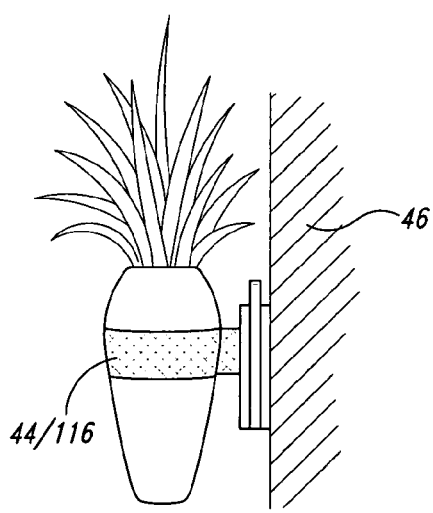

Referring also to FIGS. 29 and 30, the embodiment of FIG. 28 in which a band or belt 119 (or even rope) may be secured through the adapter plate, or even a slot with in the back plate 18 discussed above, may be worn by a person in order to attach personal or tactical items in a substantially noiseless way. In the embodiment illustrated in FIG. 30, a soldier can quickly and quietly attached or detach important tactical equipment, such as flashlight 121 (as shown). Although the flanged lip may be used, a knurled outer radius about the hold-down flange is illustrated.

The locking assembly of all embodiments may be metal, such as brushed aluminum, or a lightweight plastic or other manmade material (e.g., GE's LEXAN brand plastic) or molded from a durable polymer. The locking assembly may be of varying size per application. Additionally, more than one locking assembly may be required for certain applications.

Figure 35:
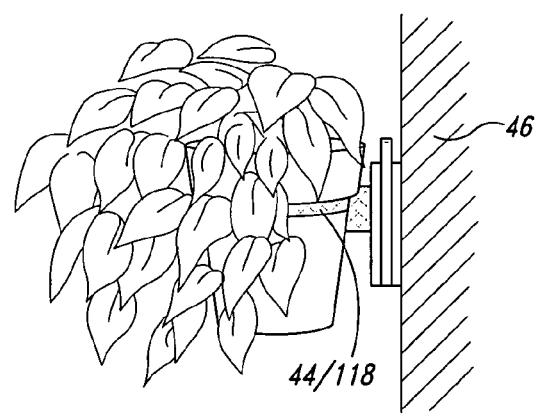
FIG. 35 is a side view of the locking assembly of FIG. 1 utilized in securing a plant pot to a solid surface.

Referring also to FIGS. 31–35, the applicability of the locking assembly of the present invention is varied. For example, the collar may be fixedly attached to a dog dish 108, as shown in FIG. 24 (or FIG. 25). Other applications may include a shelf 112 (FIGS. 31 and 32), a rod holder (e.g., a flagpole or a fishing pole holder) 114 (FIG. 33), a vase or other three-dimensional art collar 116 (FIG. 34); or a plant pot holder 118 (FIG. 35).

Referring also to FIGS. 36–39, the present invention can also be used to hang heavy framed art. In this embodiment, the locking assembly 10"" eliminates the collar previously described. In this application, the collar assembly plate 32 discussed above is attached to the back 120 of a conventional frame 122 and inserts directly into top slot 24 of the opening 22 between the front and back plates 20, 18 of the bracket assembly 12.

Advantages of the present invention include a locking assembly or mechanism that can readily attach and lock a device to a solid surface or unlock and dislodge the device from the solid surface and that the locking/dislodging action is accomplished through a single motion defined by the pivoting release lever. The locking assembly of the present invention requires no complicated stored energy mechanism. Moreover, the smooth, pivoting action in connection with the locking mechanism functions to lock a device to a solid surface in which noise is minimized. The illustrated embodiments are only examples of the present invention and, therefore, are non-limitive. It is to be understood that many changes in the particular structure, materials, and features of the invention may be made without departing from the spirit and scope of the invention. Therefore, it is the Applicant's intention that his patent rights not be limited by the particular embodiments illustrated and described herein, but rather by the following claims interpreted according to accepted doctrines of claim interpretation, including the Doctrine of Equivalents and Reversal of Parts.

What is claimed is:

1. A locking assembly for readily attaching and dislodging a device to and from a solid surface, the locking assembly comprising:
    a bracket assembly having a front plate and a back plate spaced apart and fixedly attached to each other about portions of peripheries of the front and back plates to form an opening therebetween having a top slot and an adjacent slide slot where at least a substantial portion of the top slot and the side slot are not part of the joined periphery between the front and back plate;
    a collar assembly having a collar assembly plate with an upper edge and a bottom edge; said plate being of a size and shape to be received and guided into the top slot between the front and back plates via the bottom edge of the collar assembly plate, said collar assembly further including a collar extending from a front surface of the plate and being of a size and shape to conform to an opening of the bracket assembly's front plate; said collar being fixedly attached to a device opposite where the collar is attached to the front surface of the plate;
    a pivoting release lever positioned within the side slot between the front and back plates of the bracket assembly, said pivoting release lever having an upper leg and a lower leg interconnected by a pivot that is attached to the front and back plates of the bracket assembly such that the pivoting release lever can freely pivot within the opening between the front and back plates about the pivot within a defined boundary between a locked and dislodged position and wherein the lower leg makes contact with the bottom edge of the collar assembly plate when the collar assembly plate is being locked into or dislodged from the bracket assembly;
    means for restraining pivoting movement of the pivoting release lever when the pivoting release lever is positioned to restrain movement of the plate relative to bracket assembly when the plate is substantially inserted within the opening between the front and back plates of the bracket assembly via the top slot; and
    means for securing at least the back plate of the bracket assembly to a solid surface.

2. The locking assembly according to claim 1 wherein the upper and lower legs of the pivoting release lever form a substantially L-shaped angle when joined at the pivot.

3. The locking assembly according to claim 1 wherein the means restraining movement of the pivoting release lever further includes a hold-down flange positioned proximal of the upper leg and directed inwardly toward the opening and wherein the hold down flange is sized to fit over and closely confront a portion of the upper plate of the collar assembly plate when the collar assembly plate is inserted within the top slot.

4. The locking assembly according to claim 3 wherein a notch is formed at one end of the upper edge of the collar plate assembly and that the hold-down flange of the pivoting release lever is of a shape to mate with the notch.

5. The locking assembly according to claim 3 wherein the upper leg and the hold-down flange further include an outer knurled surface.

6. The locking assembly according to claim 1 wherein the back plate of the bracket assembly is of a shape to conform to a non-planar solid surface.

7. The locking assembly according to claim 1 wherein the back plate of the bracket assembly is fixedly adjoined to an adapter plate, where the adater plate has a back surface of a shape to conform to a non-planar solid surface.

8. The locking assembly according to claim 1 wherein the means for securing the back plate to the solid surface is through at least one fastener.

9. The locking assembly according to claim 1 wherein the means for securing the back plate to the solid surface is through banding.

10. A locking assembly for readily attaching and dislodging a device to and from a solid surface, the locking assembly comprising:
   a bracket assembly having a front plate and a back plate spaced apart and fixedly attached to each other about portions of peripheries of the front and back plates to form an opening therebetween having a top slot and an adjacent slide slot where at least a substantial portion of the top slot and the side slot are not part of the joined periphery between the front and back plate;
   a collar assembly having a collar assembly plate with an upper edge and a bottom edge; said plate being of a size and shape to be received and guided into the top slot between the front and back plates via the bottom edge of the collar assembly plate, said collar assembly further including a collar extending from a front surface of the plate and being of a size and shape to conform to an opening of the bracket assembly's front plate; said collar being fixedly attached to a device opposite where the collar is attached to the front surface of the plate;
   a pivoting release lever positioned within the side slot between the front and back plates of the bracket assembly, said pivoting release lever having an upper leg and a lower leg interconnected by a pivot that is attached to the front and back plates of the bracket assembly such that the pivoting release lever can freely pivot within the opening between the front and back plates about the pivot within a defined boundary between a locked and dislodged position and wherein the lower leg makes contact with the bottom edge of the collar assembly plate when the collar assembly plate is being locked into or dislodged from the bracket assembly;
   means for restraining pivoting movement of the pivoting release lever when the pivoting release lever is positioned to restrain movement of the plate relative to bracket assembly when the plate is substantially inserted within the opening between the front and back plates of the bracket assembly via the top slot; and
   means for securing at least the back plate of the bracket assembly to a solid surface;
   wherein the upper and lower legs of the pivoting release lever form a substantially L-shaped angle when joined at the pivot, and wherein the substantially L-shaped angle between the upper and lower legs of the pivoting release lever is substantially 90 degrees.

11. A locking assembly for readily attaching and dislodging a device to and from a solid surface, the locking assembly comprising:
   a bracket assembly having a front plate and a back plate spaced apart and fixedly attached to each other about portions of peripheries of the front and back plates to form an opening therebetween having a top slot and an adjacent slide slot where at least a substantial portion of the top slot and the side slot are not part of the joined periphery between the front and back plate;
   a collar assembly having a collar assembly plate with an upper edge and a bottom edge; said plate being of a size and shape to be received and guided into the top slot between the front and back plates via the bottom edge of the collar assembly plate, said collar assembly further including a collar extending from a front surface of the plate and being of a size and shape to conform to an opening of the bracket assembly's front plate; said collar being fixedly attached to a device opposite where the collar is attached to the front surface of the plate;
   a pivoting release lever positioned within the side slot between the front and back plates of the bracket assembly, said pivoting release lever having an upper leg and a lower leg interconnected by a pivot that is attached to the front and back plates of the bracket assembly such that the pivoting release lever can freely pivot within the opening between the front and back plates about the pivot within a defined boundary between a locked and dislodged position and wherein the lower leg makes contact with the bottom edge of the collar assembly plate when the collar assembly plate is being locked into or dislodged from the bracket assembly;
   means for restraining pivoting movement of the pivoting release lever when the pivoting release lever is positioned to restrain movement of the plate relative to bracket assembly when the plate is substantially inserted within the opening between the front and back plates of the bracket assembly via the top slot; and
   means for securing at least the back plate of the bracket assembly to a solid surface;
   wherein the collar plate assembly is substantially rectangular in shape.

12. The locking assembly according to claim 11 wherein the bottom edge of the collar plate assembly is substantially rectangular in shape.

13. The locking assembly according to claim 11 wherein a notch is formed at one end of the upper edge of the collar plate assembly and that the upper leg of the pivoting release lever further includes a hold-down flange that is of a shape to mate with the notch.

14. A locking assembly for readily attaching and dislodging a device to and from a solid surface, the locking assembly comprising:
   a bracket assembly having a front plate and a back plate spaced apart and fixedly attached to each other about portions of peripheries of the front and back plates to form an opening therebetween having a top slot and an adjacent slide slot where at least a substantial portion of the top slot and the side slot are not part of the joined periphery between the front and back plate;
   a collar assembly having a collar assembly plate with an upper edge and a bottom edge; said plate being of a size and shape to be received and guided into the top slot between the front and back plates via the bottom edge of the collar assembly plate, said collar assembly further including a collar extending from a front surface of the plate and being of a size and shape to conform to an opening of the bracket assembly's front plate; said collar being fixedly attached to a device opposite where the collar is attached to the front surface of the plate;
   a pivoting release lever positioned within the side slot between the front and back plates of the bracket assembly, said pivoting release lever having an upper leg and a lower leg interconnected by a pivot that is attached to the front and back plates of the bracket assembly such that the pivoting release lever can freely pivot within the opening between the front and back plates about the pivot within a defined boundary between a locked and dislodged position and wherein the lower leg makes contact with the bottom edge of the collar assembly plate when the collar assembly plate is being locked into or dislodged from the bracket assembly;

means for restraining pivoting movement of the pivoting release lever when the pivoting release lever is positioned to restrain movement of the plate relative to bracket assembly when the plate is substantially inserted within the opening between the front and back plates of the bracket assembly via the top slot; and means for securing at least the back plate of the bracket assembly to a solid surface;

wherein the bottom edge of the collar plate assembly is substantially rectangular in shape.

15. A locking assembly for readily attaching and dislodging a device to and from a solid surface, the locking assembly comprising:

a bracket assembly having a front plate and a back plate spaced apart and fixedly attached to each other about portions of peripheries of the front and back plates to form an opening therebetween having a top slot and an adjacent slide slot where at least a substantial portion of the top slot and the side slot are not part of the joined periphery between the front and back plate;

a collar assembly having a collar assembly plate with an upper edge and a bottom edge; said plate being of a size and shape to be received and guided into the top slot between the front and back plates via the bottom edge of the collar assembly plate, said collar assembly further including a collar extending from a front surface of the plate and being of a size and shape to conform to an opening of the bracket assembly's front plate; said collar being fixedly attached to a device opposite where the collar is attached to the front surface of the plate;

a pivoting release lever positioned within the side slot between the front and back plates of the bracket assembly, said pivoting release lever having an upper leg and a lower leg interconnected by a pivot that is attached to the front and back plates of the bracket assembly such that the pivoting release lever can freely pivot within the opening between the front and back plates about the pivot within a defined boundary between a locked and dislodged position;

means for restraining pivoting movement of the pivoting release lever when the pivoting release lever is positioned to restrain movement of the plate relative to bracket assembly when the plate is substantially inserted within the opening between the front and back plates of the bracket assembly via the top slot; and means for securing at least the back plate of the bracket assembly to a solid surface;

wherein the means to restrain movement of the pivoting release lever consists of a barrel inserted within the upper leg of the pivoting release lever having an end plate at the base of the barrel of a size and shape to conform with a key having a similar conforming end to that of the end plate; and wherein the barrel further includes a flange that is moveable from side-to-side when the key is inserted into the barrel in order to engage a catch mounted within an interior side of one of the plates of the bracket assembly such that when the flange is restrained against the catch and the bracket assembly, the pivoting release lever is restrained from movement until the flange is moved away from engaging the catch.

16. A locking assembly for readily attaching and dislodging a device to and from a solid surface, the locking assembly comprising:

a bracket assembly having a front plate and a back plate spaced apart and fixedly attached to each other about portions of peripheries of the front and back plates to form an opening therebetween having a top slot and an adjacent slide slot where at least a substantial portion of the top slot and the side slot are not part of the joined periphery between the front and back plate;

a collar assembly having a collar assembly plate with an upper edge and a bottom edge; said plate being of a size and shape to be received and guided into the top slot between the front and back plates via the bottom edge of the collar assembly plate, said collar assembly further including a collar extending from a front surface of the plate and being of a size and shape to conform to an opening of the bracket assembly's front plate; said collar being fixedly attached to a device opposite where the collar is attached to the front surface of the plate;

a pivoting release lever positioned within the side slot between the front and back plates of the bracket assembly, said pivoting release lever having an upper leg and a lower leg interconnected by a pivot that is attached to the front and back plates of the bracket assembly such that the pivoting release lever can freely pivot within the opening between the front and back plates about the pivot within a defined boundary between a locked and dislodged position and wherein the lower leg makes contact with the bottom edge of the collar assembly plate when the collar assembly plate is being locked into or dislodged from the bracket assembly;

means for restraining pivoting movement of the pivoting release lever when the pivoting release lever is positioned to restrain movement of the plate relative to bracket assembly when the plate is substantially inserted within the opening between the front and back plates of the bracket assembly via the top slot; and means for securing at least the back plate of the bracket assembly to a solid surface;

wherein the collar is a cylindrical member.

17. A locking assembly for readily attaching and dislodging a device to and from a solid surface, the locking assembly comprising:

a bracket assembly having a front plate and a back plate spaced apart and fixedly attached to each other about portions of peripheries of the front and back plates to form an opening therebetween having a top slot and an adjacent slide slot where neither the top slot or side slot are part of the joined periphery between the front and back plate;

a collar assembly having a collar assembly plate with an upper edge and a bottom edge; said plate being of a size and shape to be received and guided into the top slot between the front and back plates via the bottom edge of the collar assembly plate, said collar assembly further including a collar extending from a front surface of the plate and being of a size and shape to conform to an opening of the bracket assembly's front plate; said collar being fixedly attached to a device opposite where the collar is attached to the front surface of the plate;

a pivoting release lever positioned within the side slot between the front and back plates of the bracket assembly, said pivoting release lever having an upper leg and a lower leg interconnected by a pivot that is attached to the front and back plates of the bracket assembly such that the pivoting release lever can freely pivot within the opening between the front and back plates about the pivot within a defined boundary between a locked and dislodged position and wherein the lower leg makes contact with the bottom edge of the collar assembly plate when the collar assembly plate is being locked into or dislodged from the bracket assembly;

means for restraining pivoting movement of the pivoting release lever when the pivoting release lever is positioned to restrain movement of the plate relative to bracket assembly when the plate is substantially inserted within the opening between the front and back plates of the bracket assembly via the top slot; and means for securing at least the back plate of the bracket assembly to a solid surface;

wherein the collar is a channel member having an upper wall joined by two space-apart sidewalls.

18. The locking assembly according to claim 17 wherein the channel further includes a centrally positioned wall positioned in between the two sidewalls.

19. A locking assembly for readily attaching and dislodging a device to and from a solid surface, the locking assembly comprising:

a bracket assembly having a front plate and a back plate spaced apart and fixedly attached to each other about portions of peripheries of the front and back plates to form an opening therebetween having a top slot and an adjacent slide slot where at least a substantial portion of the top slot and the side slot are not part of the joined periphery between the front and back plate and wherein at least the back plate is fixedly attached to a solid surface;

a collar assembly having a collar assembly plate with an upper edge and a bottom edge; said plate being of a size and shape to be received and guided into the top slot between the front and back plates via the bottom edge of the plate, said collar assembly further including a collar extending from a front surface of the collar assembly plate and being of a size and shape to conform to an opening of the bracket assembly's front plate; said collar being fixedly attached to a device opposite where the collar is attached to the front surface of the plate;

a pivoting release lever positioned within the side slot between the front and back plates of the bracket assembly, said pivoting release lever having an upper leg and a lower leg interconnected by a pivot that is attached to the front and back plates of the bracket assembly such that the pivoting release lever can freely pivot within the opening between the front and back plates about the pivot within a defined boundary between a locked and dislodged position, wherein the lower leg is positioned below the bottom edge of the collar assembly plate and wherein the lower leg makes contact with the bottom edge of the collar assembly plate when the collar assembly plate is being locked into or dislodged from the bracket assembly; and a hold-down flange positioned proximal of the upper leg and directed inwardly toward the opening and wherein the hold-down flange is sized to fit over and closely confront a portion of the upper plate of the collar assembly plate when the collar assembly plate is fully inserted within the top slot.

20. The locking assembly according to claim 19 wherein the upper and lower legs of the pivoting release lever form a substantially L-shaped angle when joined at the pivot.

21. The locking assembly according to claim 19 wherein a notch is formed at one end of the upper edge of the collar plate assembly and that the hold-down flange of the pivoting release lever is of a shape to mate with the notch.

22. A locking assembly for readily attaching and dislodging a device to and from a solid surface, the locking assembly comprising:

a bracket assembly having a front plate and a back plate spaced apart and fixedly attached to each other about portions of peripheries of the front and back plates to form an opening therebetween having a top slot and an adjacent slide slot where neither the top slot or side slot are part of the joined periphery between the front and back plate and wherein at least the back plate is fixedly attached to a solid surface;

a collar assembly having a collar assembly plate with an upper edge and a bottom edge; said plate being of a size and shape to be received and guided into the top slot between the front and back plates via the bottom edge of the plate, said collar assembly further including a collar extending from a front surface of the collar assembly plate and being of a size and shape to conform to an opening of the bracket assembly's front plate; said collar being fixedly attached to a device opposite where the collar is attached to the front surface of the plate;

a pivoting release lever positioned within the side slot between the front and back plates of the bracket assembly, said pivoting release lever having an upper leg and a lower leg interconnected by a pivot that is attached to the front and back plates of the bracket assembly such that the pivoting release lever can freely pivot within the opening between the front and back plates about the pivot within a defined boundary between a locked and dislodged position and wherein the lower leg makes contact with the bottom edge of the collar assembly plate when the collar assembly plate is being locked into or dislodged from the bracket assembly; and a hold-down flange positioned proximal of the upper leg and directed inwardly toward the opening and wherein the hold down flange is sized to fit over and closely confront a portion of the upper plate of the collar assembly plate when the collar assembly plate is inserted within the top slot;

wherein the upper and lower legs of the pivoting release lever form an angle when joined at the pivot and wherein the angle is substantially L-shaped.

23. A locking assembly for readily attaching and dislodging a device to and from a solid surface, the locking assembly comprising:

a bracket assembly having a front plate and a back plate spaced apart and fixedly attached to each other about portions of peripheries of the front and back plates to form an opening therebetween having a top slot and an adjacent slide slot where at least a substantial portion of the top slot and the side slot are not part of the joined periphery between the front and back plate and wherein at least the back plate is fixedly attached to a solid surface;

a collar assembly having a collar assembly plate with an upper edge and a bottom edge; said plate being of a size and shape to be received and guided into the top slot between the front and back plates via the bottom edge of the plate, said collar assembly further including a collar extending from a front surface of the collar assembly plate and being of a size and shape to conform to an opening of the bracket assembly's front plate; said collar being fixedly attached to a device opposite where the collar is attached to the front surface of the plate;

a pivoting release lever positioned within the side slot between the front and back plates of the bracket assembly, said pivoting release lever having an upper leg and a lower leg interconnected by a pivot that is attached to the front and back plates of the bracket assembly such that the pivoting release lever can freely pivot within the opening between the front and back plates about the pivot within a defined boundary between a locked and dislodged position and wherein the lower leg makes contact with the bottom edge of the collar assembly plate when the collar assembly plate is being locked into or dislodged from the bracket assembly; and a hold-down flange positioned proximal of the upper leg and directed inwardly toward the opening and wherein the hold down flange is sized to fit over and closely confront a portion of the upper plate of the collar assembly plate when the collar assembly plate is inserted within the top slot;

wherein the collar plate assembly is substantially rectangular in shape.

24. The locking assembly according to claim 23 wherein the bottom edge of the collar plate assembly is substantially rectangular in shape.

25. A locking assembly for readily attaching and dislodging a device to and from a solid surface, the locking assembly comprising:

a bracket assembly having a front plate and a back plate spaced apart and fixedly attached to each other about portions of peripheries of the front and back plates to form an opening therebetween having a top slot and an adjacent slide slot where at least a portion of the top slot and the side slot are not part of the joined periphery between the front and back plate and wherein at least the back plate is fixedly attached to a solid surface;

a collar assembly having a collar assembly plate with an upper edge and a bottom edge; said plate being of a size and shape to be received and guided into the top slot between the front and back plates via the bottom edge of the plate, said collar assembly further including a collar extending from a front surface of the collar assembly plate and being of a size and shape to conform to the opening of the bracket assembly's front plate; said collar being fixedly attached to a device opposite where the collar is attached to the front surface of the plate;

a pivoting release lever positioned within the side slot between the front and back plates of the bracket assembly, said pivoting release lever having an upper leg and a lower leg interconnected by a pivot that is attached to the front and back plates of the bracket assembly such that the pivoting release lever can freely pivot within the opening between the front and back plates about the pivot within a defined boundary between a locked and dislodged position and wherein the lower leg makes contact with the bottom edge of the collar assembly plate when the collar assembly plate is being locked into or dislodged from the bracket assembly; and a hold-down flange positioned proximal of the upper leg and directed inwardly toward the opening and wherein the hold down flange is sized to fit over and closely confront a portion of the upper plate of the collar assembly plate when the collar assembly plate is inserted within the top slot;

wherein the bottom edge of the collar plate assembly is substantially rectangular in shape.

26. A locking assembly for readily attaching and dislodging a device to and from a solid surface, the locking assembly comprising:

a bracket assembly having a front plate and a back plate spaced apart and fixedly attached to each other about portions of peripheries of the front and back plates to form an opening therebetween having a top slot and an adjacent slide slot where at least a substantial portion of the top slot and the side slot are not part of the joined periphery between the front and back plate, and wherein at least the back plate is fixedly attached to a solid surface;

a collar assembly having a collar assembly plate with an upper edge and a bottom edge; said plate being of a size and shape to be received and guided into the top slot between the front and back plates via the bottom edge of the collar assembly plate, said collar assembly further including a collar extending from a front surface of the plate and being of a size and shape to conform to the opening of the bracket assembly; said collar being fixedly attached to a device opposite where the collar is attached to the front surface of the plate;

a pivoting release lever positioned within the side slot between the front and back plates of the bracket assembly, said pivoting release lever having an upper leg and a lower leg interconnected by a pivot that is attached to the front and back plates of the bracket assembly such that the pivoting release lever can freely pivot within the opening between the front and back plates about the pivot within a defined boundary between a locked and dislodged position;

wherein the pivoting release lever further consists of a barrel inserted within the upper leg of the pivoting release lever having an end plate at the base of the barrel of a size and shape to conform with a key having a similar conforming end to that of the base; and wherein the barrel further includes a flange that is moveable from side-to-side when the key is inserted into the barrel in order to engage a catch mounted within an interior side of one of the plates of the bracket assembly such that when the flange is restrained against the catch and the bracket assembly, the pivoting release lever is restrained from movement until the flange is moved away from engaging the catch.

27. A locking assembly for readily attaching and dislodging a device to and from a solid surface, the combination of the locking assembly and device comprising:

a bracket assembly having a front plate and a back plate spaced apart and fixedly attached to each other about portions of peripheries of the front and back plates to form an opening therebetween having a top slot and an adjacent slide slot where at least a portion of the top slot and the side slot are not part of the joined periphery between the front and back plate;

a collar assembly having a collar assembly plate with an upper edge and a bottom edge; said plate being of a size and shape to be received and guided into the top slot between the front and back plates via the bottom edge of the collar assembly plate, said collar assembly being fixedly attached to a device;

a pivoting release lever positioned within the side slot between the front and back plates of the bracket assembly, said pivoting release lever having an upper leg and a lower leg interconnected by a pivot that is attached to the front and back plates of the bracket assembly such that the pivoting release lever can freely pivot within the opening between the front and back plates about the pivot within a defined boundary between a locked and dislodged position, the lower leg makes contact with the bottom edge of the collar assembly plate when the collar assembly plate is being locked into or dislodged from the bracket assembly and;

means for restraining pivoting movement of the pivoting release lever when the pivoting release lever is positioned to restrain movement of the plate relative to bracket assembly with springs when the plate is substantially inserted within the opening between the front and back plates of the bracket assembly via the top slot; and means for securing at least the back plate of the bracket assembly to a solid surface.

28. The locking assembly according to claim 27 wherein the device is a dog dish.

29. The locking assembly according to claim 27 wherein the device is a shelf.

30. The locking assembly according to claim 27 wherein the device is a rod holder.

31. The locking assembly according to claim 27 wherein the device is a collar.

32. The locking assembly according to claim 27 wherein the device is a framed piece of art and the back of the frame includes the collar assembly plate.

33. The locking assembly according to claim 27 wherein the device is a flashlight.

34. The locking assembly according to claim 27 wherein the means restraining movement of the pivoting release lever further includes a hold-down flange positioned proximal of the upper leg and directed inwardly toward the opening and wherein the hold-down flange is sized to fit over and closely confront a portion of the upper the hold-down flange is sized to fit over and closely confront a portion of the upper plate of the collar assembly plate when the collar assembly plate is inserted within the top slot.

35. The locking assembly according to claim 34 wherein a notch is formed at one end of the upper edge of the collar plate assembly and that the hold-down flange of the pivoting release lever is of a shape to mate with the notch.

* * * * *

UNITED STATES PATENT AND TRADEMARK OFFICE
CERTIFICATE OF CORRECTION

PATENT NO.        : 7,077,372 B2
APPLICATION NO.   : 10/996551
DATED             : July 18, 2006
INVENTOR(S)       : Eric M. Moran It is certified that error appears in the above-identified patent and that said Letters Patent is hereby corrected as shown below:

Col. 5, line 48: Please replace "separated" with -- separate --
Col. 6, line 24: Please insert -- 62 -- after the word "notch"
Col. 7, line 6: Please insert -- , -- after the number "66"
Col. 7, line 6: Please insert -- a -- after the word "in"
Col. 7, line 7: Please replace "extending" with -- external --
Col. 7, line 11: Please replace "flange" with -- flanged --

Claim 27, Col. 19, line 4: Please insert -- the -- before the word "bracket assembly"
Claim 27, Col. 19, line 4: Please delete the words "with springs"
Claim 34, Col. 20, line 4: Please insert -- for -- after the word "means"
Claim 34, Col. 20, lines 9 through 11: Please delete the extraneous words "the hold-down flange is sized to fit over and closely confront a portion of the upper" after the word "upper" in line 9.

Signed and Sealed this

Seventeenth Day of April, 2007

JON W. DUDAS
*Director of the United States Patent and Trademark Office*

UNITED STATES PATENT AND TRADEMARK OFFICE
CERTIFICATE OF CORRECTION

PATENT NO. : 7,077,372 B2  Page 1 of 1
APPLICATION NO. : 10/996551
DATED : July 18, 2006
INVENTOR(S) : Eric M. Moran It is certified that error appears in the above-identified patent and that said Letters Patent is hereby corrected as shown below:

Claim 1, Col. 10, line 9: Please replace "slide" with -- side --
Claim 10, Col. 11, line 14: Please replace "slide" with -- side --
Claim 11, Col. 11, line 59: Please replace "slide" with -- side --
Claim 14, Col. 12, line 43: Please replace "slide" with -- side --
Claim 15, Col. 13, line 18: Please replace "slide" with -- side --
Claim 16, Col. 14, line 2: Please replace "slide" with -- side --
Claim 17, Col. 14, line 43: Please replace "slide" with -- side --
Claim 19, Col. 15, line 21: Please replace "slide" with -- side --
Claim 22, Col. 16, line 5: Please replace "slide" with -- side --
Claim 23, Col. 16, line 48: Please replace "slide" with -- side --
Claim 25, Col. 17, line 27: Please replace "slide" with -- side --
Claim 26, Col. 18, line 2: Please replace "slide" with -- side --
Claim 27, Col. 18, line 47: Please replace "slide" with -- side --

Signed and Sealed this

First Day of January, 2008

JON W. DUDAS
*Director of the United States Patent and Trademark Office*